US012697352B2

(12) United States Patent
Alster et al.

(10) Patent No.: US 12,697,352 B2
(45) Date of Patent: *Aug. 4, 2026

(54) INSTRUCTIONS FOR COMPOSITION AND SENSITIVITY

(71) Applicant: Azura Ophthalmics Ltd., Tel Aviv (IL)

(72) Inventors: Yair Alster, Tel Aviv (IL); Charles Bosworth, Las Vegas, NV (US); Hila Epstein-Barash, Shoham (IL); Omer Rafaeli, Udim (IL)

(73) Assignee: Azura Ophthalmics Ltd., Tel Aviv (IL)

( * ) Notice: Subject to any disclaimer, the term of this patent is extended or adjusted under 35 U.S.C. 154(b) by 524 days.

This patent is subject to a terminal disclaimer.

(21) Appl. No.: 18/075,161

(22) Filed: Dec. 5, 2022

(65) Prior Publication Data

US 2023/0346832 A1 Nov. 2, 2023

Related U.S. Application Data

(63) Continuation of application No. 17/471,111, filed on Sep. 9, 2021, now Pat. No. 11,517,586, which is a continuation of application No. PCT/IB2021/000005, filed on Jan. 7, 2021.

(60) Provisional application No. 62/959,738, filed on Jan. 10, 2020.

(51) Int. Cl.
| | |
|---|---|
| *A61K 33/04* | (2006.01) |
| *A61K 9/00* | (2006.01) |
| *A61K 9/06* | (2006.01) |
| *A61P 27/02* | (2006.01) |

(52) U.S. Cl.
CPC ............ *A61K 33/04* (2013.01); *A61K 9/0048* (2013.01); *A61K 9/06* (2013.01); *A61P 27/02* (2018.01)

(58) Field of Classification Search
CPC ........ A61K 33/04; A61K 9/0048; A61K 9/06; A61P 27/02
See application file for complete search history.

(56) References Cited

U.S. PATENT DOCUMENTS

| | | | |
|---|---|---|---|
| 2,209,192 | A | 7/1940 | Demsey |
| 3,236,730 | A | 2/1966 | Galin |
| 3,279,466 | A | 10/1966 | Mings |
| 3,439,674 | A | 4/1969 | Lelicoff |
| 3,934,590 | A | 1/1976 | Campagna et al. |
| 4,002,168 | A | 1/1977 | Petterson |
| 4,085,750 | A | 4/1978 | Bosshold |
| 4,512,977 | A | 4/1985 | Lundy |
| 4,531,944 | A | 7/1985 | Bechtle |
| 4,543,096 | A | 9/1985 | Keene |
| 4,605,398 | A | 8/1986 | Herrick |
| 4,733,802 | A | 3/1988 | Sheldon |
| 4,792,334 | A | 12/1988 | Py |
| 4,834,727 | A | 5/1989 | Cope |
| 4,838,851 | A | 6/1989 | Shabo |
| 4,909,801 | A | 3/1990 | Casey et al. |
| 4,946,452 | A | 8/1990 | Py |
| 4,960,407 | A | 10/1990 | Cope |
| 4,981,479 | A | 1/1991 | Py |
| 5,007,905 | A | 4/1991 | Bauer |
| 5,037,406 | A | 8/1991 | Smith et al. |
| 5,059,188 | A | 10/1991 | Goddard |
| 5,133,702 | A | 7/1992 | Py |
| 5,221,027 | A | 6/1993 | Gibilsco |
| 5,267,986 | A | 12/1993 | Py |
| 5,330,757 | A | 7/1994 | Burke |
| 5,366,448 | A | 11/1994 | Basilice et al. |
| 5,382,243 | A | 1/1995 | Mulholland |
| 5,387,202 | A | 2/1995 | Baron |
| 5,401,259 | A | 3/1995 | Py |
| 5,578,019 | A | 11/1996 | Feldman |
| 5,645,827 | A | 7/1997 | Marlin et al. |
| 5,810,794 | A | 9/1998 | Peplinski |
| 5,922,349 | A | 7/1999 | Elliesen et al. |
| 6,010,488 | A | 1/2000 | Deas |
| 6,011,067 | A | 1/2000 | Hersh |
| 6,033,384 | A | 3/2000 | Py |
| 6,090,086 | A | 7/2000 | Bolden |
| 6,153,607 | A | 11/2000 | Pflugfelder et al. |
| 6,348,508 | B1 | 2/2002 | Denick, Jr. et al. |
| 6,371,945 | B1 | 4/2002 | Sherman |
| 6,495,158 | B1 | 12/2002 | Buseman et al. |

(Continued)

FOREIGN PATENT DOCUMENTS

| | | |
|---|---|---|
| CH | 630801 A5 | 7/1982 |
| CH | 679912 A5 | 5/1992 |

(Continued)

OTHER PUBLICATIONS 1.2.2 Congealing point. The International Pharmacopoeia 2019, retrieved from https://apps.who.int/phint/pdf/b/7.1.2.2.1.2.2-Congealing-point.pdf.

Aimsizer. 101-What is D90. Oct. 29, 2019 retrieved from http://www.aimsizer.com/faqs-what-is-d90.html.

Akyol-Salman et al. Efficacy of topical N-acetylcysteine in the treatment of meibomian gland dysfunction. J Ocul Pharmacol Ther 26(4):329-333 (2010).

Anonymous. Ointments and Types of ointment bases. Pharmaceutical Drugs and Dosage: Semisolid dosage forms. Available at https://www.pharmacy180.com/article/ointments-and-types-of-ointment-bases-2856/ (2019).

Bahn. The treatment of seborrheic blepharitis. South Med 47(8):749-53 (1954).

(Continued)

*Primary Examiner* — Zohreh A Fay
(74) *Attorney, Agent, or Firm* — Faegre Drinker Biddle & Reath LLP

(57) ABSTRACT

Provided herein are methods treating a disease or disorder in or around the eye with a pharmaceutical composition comprising selenium disulfide (SeS$_2$) and instructing the treated individual to limit or avoid exposure to light following administration in order to reduce the adverse effect of the composition.

32 Claims, 1 Drawing Sheet

(56)                    References Cited

U.S. PATENT DOCUMENTS

| | | | |
|---|---|---|---|
| 6,508,793 B1 | 1/2003 | Harrold |
| 6,530,908 B1 | 3/2003 | Sherman et al. |
| 7,235,065 B1 | 6/2007 | Sorensen |
| 7,288,259 B2 | 10/2007 | Sanders et al. |
| 7,325,708 B2 | 2/2008 | Barber |
| 7,776,915 B2 | 8/2010 | Morariu |
| 8,206,362 B1 | 6/2012 | Crosswell, Jr. |
| 8,216,195 B2 | 7/2012 | Wu |
| 8,246,589 B2 | 8/2012 | Marx |
| 8,420,699 B1 | 4/2013 | Dubow |
| 8,449,928 B2 | 5/2013 | Gilbard et al. |
| 8,455,016 B2 | 6/2013 | Maskin |
| 8,734,408 B2 | 5/2014 | Marx |
| 8,853,247 B2 | 10/2014 | Ren et al. |
| 9,072,581 B1 | 7/2015 | Alam et al. |
| 9,205,241 B2 | 12/2015 | McKay |
| 9,463,201 B2 | 10/2016 | Alster et al. |
| 10,034,887 B2 | 7/2018 | Alster et al. |
| 10,213,336 B2 | 2/2019 | Lorch et al. |
| 10,299,959 B2 | 5/2019 | Behan |
| 10,383,790 B2 | 8/2019 | Barkholt et al. |
| 10,558,915 B2 | 2/2020 | Gao et al. |
| 10,588,915 B2 | 3/2020 | Alster et al. |
| 10,688,122 B2 | 6/2020 | Amselem et al. |
| 10,772,889 B2 | 9/2020 | Johns et al. |
| 10,772,899 B2 | 9/2020 | Alster et al. |
| 11,013,749 B2 | 5/2021 | Alster et al. |
| 11,040,062 B2 | 6/2021 | Friedman et al. |
| 11,103,749 B2 | 8/2021 | Mermel et al. |
| 11,324,775 B2 | 5/2022 | Bosworth et al. |
| 11,484,516 B2 | 11/2022 | Amselem et al. |
| 11,517,386 B2 | 12/2022 | Luo et al. |
| 11,517,586 B2 | 12/2022 | Alster et al. |
| 11,633,410 B2 | 4/2023 | Alster et al. |
| 12,048,707 B2 | 7/2024 | Alster et al. |
| 12,083,147 B2 | 9/2024 | Bosworth et al. |
| 2002/0127256 A1 | 9/2002 | Murad |
| 2003/0180339 A1 | 9/2003 | Khaiat et al. |
| 2003/0224028 A1 | 12/2003 | Galey |
| 2003/0228299 A1 | 12/2003 | Droy-Lefaix et al. |
| 2004/0171561 A1 | 9/2004 | Popp |
| 2004/0192647 A1 | 9/2004 | Babizhayev |
| 2004/0220167 A1 | 11/2004 | Samiy |
| 2005/0065091 A1 | 3/2005 | Peyman |
| 2005/0101921 A1 | 5/2005 | Sherman |
| 2005/0124690 A1 | 6/2005 | Yoon et al. |
| 2005/0197614 A1 | 9/2005 | Pritchard et al. |
| 2006/0081726 A1 | 4/2006 | Gerondale |
| 2006/0110428 A1 | 5/2006 | Dejuan et al. |
| 2006/0129113 A1 | 6/2006 | Merrick |
| 2006/0157516 A1 | 7/2006 | Barber |
| 2006/0188471 A1 | 8/2006 | Podolsky et al. |
| 2006/0216251 A1 | 9/2006 | Morariu |
| 2007/0082017 A1 | 4/2007 | Tseng et al. |
| 2007/0104758 A1 | 5/2007 | Hamilton et al. |
| 2007/0166402 A1 | 7/2007 | Friedlaender et al. |
| 2007/0208181 A1 | 9/2007 | Lauener et al. |
| 2007/0269537 A1 | 11/2007 | Gupta |
| 2007/0280924 A1 | 12/2007 | Daniels et al. |
| 2007/0292355 A1 | 12/2007 | Tamarkin et al. |
| 2008/0020044 A1 | 1/2008 | Alam et al. |
| 2008/0025929 A1 | 1/2008 | Burton et al. |
| 2008/0081996 A1 | 4/2008 | Grenon et al. |
| 2008/0103376 A1 | 5/2008 | Felder |
| 2008/0114420 A1 | 5/2008 | Korb et al. |
| 2008/0242729 A1 | 10/2008 | Bollag |
| 2008/0318939 A1* | 12/2008 | Whitten ................. A61P 27/00 |
| | | 514/253.02 |
| 2009/0061025 A1 | 3/2009 | Gao et al. |
| 2009/0123527 A1 | 5/2009 | Alam et al. |
| 2009/0214676 A1 | 8/2009 | Gao et al. |
| 2009/0238810 A1 | 9/2009 | Nyunt |
| 2009/0259204 A1 | 10/2009 | Galdeti et al. |
| 2009/0281508 A1 | 11/2009 | Alvino |
| 2010/0034870 A1 | 2/2010 | Sim et al. |
| 2010/0113338 A1 | 5/2010 | Watanabe et al. |
| 2010/0152201 A1 | 6/2010 | Riggs-Sauthier et al. |
| 2010/0204317 A1 | 8/2010 | Hunt et al. |
| 2010/0256552 A1 | 10/2010 | Korb et al. |
| 2010/0285155 A1 | 11/2010 | Gilbard et al. |
| 2011/0022010 A1 | 1/2011 | Grenon et al. |
| 2011/0059925 A1 | 3/2011 | Donnenfeld |
| 2011/0104206 A1 | 5/2011 | Nanduri et al. |
| 2011/0124725 A1 | 5/2011 | Maskin |
| 2011/0130729 A1 | 6/2011 | Korb et al. |
| 2011/0137214 A1 | 6/2011 | Korb et al. |
| 2011/0218241 A1 | 9/2011 | Preston et al. |
| 2011/0294897 A1 | 12/2011 | Aberg et al. |
| 2012/0016275 A1 | 1/2012 | Korb et al. |
| 2012/0028929 A1 | 2/2012 | Power et al. |
| 2012/0093876 A1 | 4/2012 | Ousler, III et al. |
| 2012/0128763 A1 | 5/2012 | Maskin |
| 2012/0150132 A1 | 6/2012 | Cress |
| 2012/0190661 A1 | 7/2012 | Trogden et al. |
| 2012/0226156 A1 | 9/2012 | Grenon et al. |
| 2012/0264681 A1 | 10/2012 | Braiman-Wiksman et al. |
| 2012/0288575 A1 | 11/2012 | Gilbard et al. |
| 2012/0310184 A1 | 12/2012 | Pedersen |
| 2013/0006202 A1 | 1/2013 | Marx |
| 2013/0053733 A1 | 2/2013 | Korb et al. |
| 2013/0064788 A1 | 3/2013 | Barnes et al. |
| 2013/0131171 A1 | 5/2013 | Maskin |
| 2013/0184242 A1 | 7/2013 | Eini et al. |
| 2013/0224272 A1 | 8/2013 | Gao et al. |
| 2013/0274214 A1 | 10/2013 | Brubaker |
| 2013/0280340 A1 | 10/2013 | Dobbie |
| 2013/0281390 A1 | 10/2013 | Brubaker |
| 2013/0303502 A1 | 11/2013 | Cavanagh et al. |
| 2013/0331768 A1 | 12/2013 | Nichamin |
| 2013/0344128 A1 | 12/2013 | Gao et al. |
| 2013/0345185 A1 | 12/2013 | Mitra et al. |
| 2014/0005171 A1 | 1/2014 | Aukunuru et al. |
| 2014/0010855 A1 | 1/2014 | Mahadevan et al. |
| 2014/0017886 A1 | 1/2014 | Teo et al. |
| 2014/0058340 A1 | 2/2014 | Guillon et al. |
| 2014/0142055 A1 | 5/2014 | Hosseini et al. |
| 2014/0142668 A1 | 5/2014 | Guillon et al. |
| 2014/0154333 A1 | 6/2014 | Moloney |
| 2014/0171884 A1 | 6/2014 | Rehkemper et al. |
| 2014/0171886 A1 | 6/2014 | Ogawa et al. |
| 2014/0206708 A1 | 7/2014 | Ren et al. |
| 2014/0350490 A1 | 11/2014 | Korodi |
| 2015/0025506 A1 | 1/2015 | Chau |
| 2015/0080349 A1 | 3/2015 | Blackwell et al. |
| 2015/0190279 A1 | 7/2015 | Acharya et al. |
| 2015/0265565 A1 | 9/2015 | O'Haimhirgin |
| 2015/0328044 A1 | 11/2015 | Coop et al. |
| 2015/0328290 A1 | 11/2015 | Leren et al. |
| 2016/0038339 A1 | 2/2016 | Behan |
| 2016/0106775 A1 | 4/2016 | Alster et al. |
| 2016/0199405 A1 | 7/2016 | Sutich |
| 2017/0035785 A1 | 2/2017 | Alster et al. |
| 2017/0087179 A1 | 3/2017 | Amselem et al. |
| 2017/0196732 A1 | 7/2017 | Marx |
| 2017/0224532 A1 | 8/2017 | Behan |
| 2017/0312364 A1 | 11/2017 | Bossy et al. |
| 2018/0043024 A1 | 2/2018 | Sakurai et al. |
| 2018/0177391 A1 | 6/2018 | Korb et al. |
| 2018/0250224 A1 | 9/2018 | Yamamoto et al. |
| 2018/0303906 A1 | 10/2018 | Caspi et al. |
| 2018/0318313 A1 | 11/2018 | Sengupta et al. |
| 2018/0344512 A1 | 12/2018 | Badawi |
| 2019/0167523 A1 | 6/2019 | Browka et al. |
| 2019/0183676 A1 | 6/2019 | Eaton et al. |
| 2019/0231788 A1 | 8/2019 | Godessart Marina et al. |
| 2019/0358083 A1 | 11/2019 | Barash |
| 2020/0179305 A1 | 6/2020 | Alster et al. |
| 2020/0179440 A1 | 6/2020 | Amselem et al. |
| 2020/0276048 A1 | 9/2020 | Hossain et al. |
| 2020/0330488 A1 | 10/2020 | Alster et al. |
| 2021/0161707 A1 | 6/2021 | Alster et al. |
| 2021/0236518 A1 | 8/2021 | Alster et al. |
| 2021/0330703 A1 | 10/2021 | Friedman et al. |
| 2021/0378863 A1 | 12/2021 | Gamboa Burgos |

(56) References Cited

U.S. PATENT DOCUMENTS

| | | | |
|---|---|---|---|
| 2022/0226367 A1 | 7/2022 | Amselem et al. | |
| 2022/0233350 A1 | 7/2022 | Van Gorden et al. | |
| 2022/0233584 A1 | 7/2022 | Bosworth et al. | |
| 2022/0305052 A1 | 9/2022 | Alster et al. | |
| 2022/0323487 A1 | 10/2022 | Rafaeli et al. | |
| 2022/0347207 A1 | 11/2022 | Epstein-Barash et al. | |
| 2022/0388737 A1 | 12/2022 | Gamboa Burgos | |
| 2022/0409657 A1 | 12/2022 | Alster et al. | |
| 2023/0000675 A1 | 1/2023 | Alster et al. | |
| 2023/0013824 A1 | 1/2023 | Alster et al. | |
| 2023/0218642 A1 | 7/2023 | Alster et al. | |
| 2024/0285679 A1 | 8/2024 | Bosworth et al. | |
| 2024/0299445 A1 | 9/2024 | Friedman et al. | |

FOREIGN PATENT DOCUMENTS

| | | | |
|---|---|---|---|
| CN | 1093897 A | 10/1994 | |
| CN | 101132693 A | 2/2008 | |
| CN | 101418020 A | 4/2009 | |
| CN | 101612161 A | 12/2009 | |
| CN | 102038953 A | 5/2011 | |
| CN | 103037802 A | 4/2013 | |
| CN | 105439958 A | 3/2016 | |
| CN | 105456287 A | 4/2016 | |
| CN | 205459330 U | 8/2016 | |
| CN | 106727285 A | 5/2017 | |
| CN | 104936565 B | 6/2017 | |
| CN | 109310665 A | 2/2019 | |
| CN | 114989375 A | 9/2022 | |
| EP | 0925799 A2 | 6/1999 | |
| EP | 0930072 A1 | 7/1999 | |
| EP | 1621191 A1 | 2/2006 | |
| EP | 1915998 A1 | 4/2008 | |
| EP | 2633852 A1 | 9/2013 | |
| EP | 2664330 A1 | 11/2013 | |
| EP | 2667877 A2 | 12/2013 | |
| EP | 3206497 A1 | 8/2017 | |
| ES | 283484 U | 5/1985 | |
| JP | H069383 A | 1/1994 | |
| JP | H07233057 A | 9/1995 | |
| JP | H1171272 A | 3/1999 | |
| JP | H11292793 A | 10/1999 | |
| JP | 2010510961 A | 4/2010 | |
| JP | 2010520210 A | 6/2010 | |
| JP | 2013507132 A | 3/2013 | |
| JP | 2014518275 A | 7/2014 | |
| JP | 2015514722 A | 5/2015 | |
| JP | 2016520335 A | 7/2016 | |
| JP | 6501096 B1 | 4/2019 | |
| KR | 19990063155 A | 7/1999 | |
| KR | 101181302 B1 | 9/2012 | |
| NL | 7804368 A | 10/1979 | |
| WO | WO-9611686 A1 | 4/1996 | |
| WO | WO-9724116 A2 | 7/1997 | |
| WO | WO-9824504 A2 | 6/1998 | |
| WO | WO-03035076 A1 | 5/2003 | |
| WO | WO-03050190 A2 | 6/2003 | |
| WO | WO-2005067892 A1 | 7/2005 | |
| WO | WO-2006137426 A1 | 12/2006 | |
| WO | WO-2007070463 A2 | 6/2007 | |
| WO | WO-2007113830 A2 | 10/2007 | |
| WO | WO-2007133703 A2 | 11/2007 | |
| WO | WO-2008027069 A1 | 3/2008 | |
| WO | WO-2008041177 A2 | 4/2008 | |
| WO | WO-2008068866 A1 | 6/2008 | |
| WO | WO-2008106228 A2 | 9/2008 | |
| WO | WO-2010006117 A2 | 1/2010 | |
| WO | WO-2011006079 A2 | 1/2011 | |
| WO | WO-2012092320 A2 | 7/2012 | |
| WO | WO-2012155062 A1 | 11/2012 | |
| WO | WO-2012161112 A1 | 11/2012 | |
| WO | WO-2013003731 A2 | 1/2013 | |
| WO | WO-2014078956 A1 | 5/2014 | |
| WO | WO-2014106759 A1 | 7/2014 | |
| WO | WO-2015017316 A2 | 2/2015 | |
| WO | WO-2015022546 A1 | 2/2015 | |
| WO | WO-2015054075 A1 | 4/2015 | |
| WO | WO-2015169728 A1 | 11/2015 | |
| WO | WO-2016063130 A1 | 4/2016 | |
| WO | WO-2016196989 A1 | 12/2016 | |
| WO | WO-2017055924 A2 | 4/2017 | |
| WO | WO-2017178892 A2 | 10/2017 | |
| WO | WO-2017182885 A2 | 10/2017 | |
| WO | WO-2018044758 A1 | 3/2018 | |
| WO | WO-2018178769 A1 | 10/2018 | |
| WO | WO-2020030975 A2 | 2/2020 | |
| WO | WO-2020208418 A1 | 10/2020 | |
| WO | WO-2020212760 A2 | 10/2020 | |
| WO | WO-2020247594 A1 | 12/2020 | |
| WO | WO-2021090058 A2 | 5/2021 | |
| WO | WO-2021090070 A2 | 5/2021 | |
| WO | WO-2021136968 A2 | 7/2021 | |
| WO | WO-2021140417 A2 | 7/2021 | |
| WO | WO-2021140419 A1 | 7/2021 | |
| WO | WO-2022084738 A2 | 4/2022 | |
| WO | WO-2022084739 A1 | 4/2022 | |
| WO | WO-2022084747 A1 | 4/2022 | |
| WO | WO-2022269348 A1 | 12/2022 | |
| WO | WO-2023043743 A1 | 3/2023 | |
| WO | WO-2023067387 A2 | 4/2023 | |
| WO | WO-2024100454 A2 | 5/2024 | |
| WO | WO-2024134266 A1 | 6/2024 | |
| WO | WO-2024134272 A2 | 6/2024 | |
| WO | WO-2025012700 A2 | 1/2025 | |
| WO | WO-2025012701 A2 | 1/2025 | |

OTHER PUBLICATIONS

Barrault et al. Immortalized sebocytes can spontaneously differentiate into a sebaceous-like phenotype when cultured as a 3D epithelium. Exp Dermatol 21:299-319 (2012).

Berge et al. Pharmaceutical Salts. Journal of Pharmaceutical Sciences 66(1):1-19 (Jan. 1977).

Butovich et al. Human tear film and meibum. Very long chain wax esters and (O-acyl)-omega-hydroxy fatty acids of meibum. J Lipid Res 50(12):2471-2485 (2009).

Chalmers et al. Contact Lens Dry Eye Questionnaire-8 (CLDEQ-8) and opinion of contact lens performance. Optom Vis Sci. 89:1435-1442 (2012).

Chalmers et al. Contact Lens Dry Eye Questionnaire-8 (CLDEQ-8): Use of an 8-Item Habitual Symptom Score to Reflect Change in Overall Opinion on Contact Lens Performance. Invest Ophthalmol Vis Sci 50:6337 (2009).

Chalmers et al. Cutoff score and responsiveness of the 8-item Contact Lens Dry Eye Questionnaire (CLDEQ-8) in a Large daily disposable contact lens registry. Cont. Lens. Anterior Eye. 39(5):342-52 (2016).

Charlton et al. Topical urea as a treatment for non-infectious keratopathy. Acta Ophthalmol Scand 74(4):391-394 (1996).

Chew et al. An instrument for quantifying meibomian lipid on the lid margin: the Meibometer. Curr Eye Res 12(3):247-254 (1993).

Chougule et al. Synthesis, Characterization And Anthelmintic Activity Of Ivermectin Analogues Of Potent Nsaids. IAJPR 11(8):2035-2041 (2021).

Chowhan et al., Ophthalmic Preparations. Remington p. 541 (2012).

De Villiers. Chapter 23: Ointment Base. A Practical Guide to Contemporary Pharmacy Practice. Publisher: Wolters Kluwer Health/ Lippincott Williams & Wilkins. Editors: Judith E. Thompson (pp. 277-290) (2009).

Driver et al. Meibomian Gland Dysfunction. Survey of Ophthalmology 40(5):343-367 (1996).

Efron et al. Lid Wiper Epitheliopathy. Prog Retin Eye Res. 53:140-174 (2016).

Foulks et al. The TFOS International Workshop on Contact Lens Discomfort: Report of the Subcommittee on Clinical Trial Design and Outcomes. Invest Ophthalmol Vis Sci 54:TFOS157-TFOS182 (2013).

Geerling et al., The International Workshop on Meibomian Gland Dysfunction: Report of the Subcommittee on Management and

(56) References Cited

OTHER PUBLICATIONS

Treatment of Meibomian Gland Dysfunction. The Association for Research in Vision and Ophthalmology, Inc., IOVS Special Issue 2011, 52(4):2050-2064 (2011).

Gonzalez-Hinojosa et al. Demodex and Rosacea: Is there a relationship? Ind. J Ophthalmol. 66(1):36-38 (2018).

Heiligenhaus et al. Therapy of dry eye disorders [Therapie von Benetzungsstorungen]. Klin Monatsbl Augenheilkd 204:162-168 (1994) (English Summary).

Higuchi et al. Selenium compound protects corneal epithelium against oxidative stress. PLoS One 7(9):e45612 (2012).

Itoh et al. The Molecular Mechanism of the Synthesis of the 21st Amino Acid, Selenocysteine. Journal of Japanese Crystal Society 56(3):186-193 (2014) (English Abstract).

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Knop et al., The lid wiper and muco-cutaneous junction anatomy of the human eyelid margins: an in vivo confocal and histological study. Journal of Anatomy 218(4):449-461 (2011).

Koenig et al. Organic Sulfur Derivatives. V.2 Preparation and Properties of Some Long-Chain Mercapto Acids and Related Compounds. J Org Chem 23:1525-1530 (1958).

Korb et al. Meibomian gland dysfunction and contact lens intolerance. J Am Optom Assoc 51(3):243-251 (1980).

Lavyel. Selsunef ointment to treat squamous blepharitis. Am J Ophthalmol 49:820-821 (1960).

Lin et al. In vitro and in vivo percutaneous absorption of seleno-L-methionine, an antioxidant agent, and other selenium species. Acta Pharmacol Sin 32(9):1181-1190 (2011).

L-Selenomethionine—Safety Data Sheet. Cayman Chemical Revision Sep. 8, 2018.

Maskin. Intraductal meibomian gland probing relieves symptoms of obstructive meibomian gland dysfunction. Cornea 29(10):1145-1152 (2010).

Millar et al. The effect of dietary and pharmacological manipulation of lipid production in the Meibomian and Harderian glands of the rabbit. Lacrimal Gland, Tear Film, and Dry Eye Syndromes 3. Advances in Experimental Medicine and Biology 506:431-440 (2002).

Nagymihalyi et al. The influence of eyelid temperature on the delivery of Meibomian oil. Exp Eye Res 78:367-370 (2004).

Nederfors et al. Effects of the antihypertensive drug captopril on human salivary secretion rate and composition. Eur J Oral Sci 103(6):351-354 ( Dec. 1995) (Abstract).

Nelson et al. The International Workshop on Meibomian Gland Dysfunction: Report of the Definition and Classification Subcommittee. Invest Ophthalmol Vis Sci. 52(4):1930-1937 (2011).

Nichols et al. Dual-Polymer Drops, Contact Lens Comfort, and Lid Wiper Epitheliopathy. Optom Vis Sci. 93(8):979-86 (2016).

Nichols et al. The Performance of the Contact Lens Dry Eye Questionnaire as a Screening Survey for Contact Lens-related Dry Eye. Cornea 21(5):469-475 (2002).

Nichols. The International Workshop on Meibomian Gland Dysfunction: Introduction. Invest Ophthalmol Vis Sci 52(4):1917-1921 (2011).

Omali et al. Quantification of individual proteins in silicone hydrogel contact lens deposits. Mol Vis. 19:390-399 (2013).

PCT/IB2015/02164 International Search Report and Written Opinion dated Mar. 29, 2016.

PCT/IB2017/000638 International Search Report and Written Opinion dated Oct. 30, 2017.

PCT/IB2017/00542 International Search Report and Written Opinion dated Sep. 21, 2017.

PCT/IB2018/000415 International Search Report and Written Opinion dated Aug. 30, 2018.

PCT/IB2019/000903 International Search Report and Written Opinion dated Feb. 27, 2020.

PCT/IB2019/000903 Invitation to Pay Additional Fees dated Dec. 31, 2019.

PCT/IB2020/000262 International Search Report and Written Opinion dated Aug. 12, 2020.

PCT/IB2020/000907 International Invitation to Pay Additional Fees dated May 5, 2021.

PCT/IB2020/001094 International Invitation to Pay Additional Fees dated May 5, 2021.

PCT/IB2020/00907 International Search Report and Written Opinion dated Jul. 21, 2021.

PCT/IB2020/00980 International Search Report and Written Opinion dated May 12, 2021.

PCT/IB2020/01094 International Search Report and Written Opinion dated Jul. 27, 2021.

PCT/IB2021/00005 International Invitation to Pay Additional Fees dated May 18, 2021.

PCT/IB2021/00005 International Search Report and Written Opinion dated Jul. 22, 2021.

PCT/IB2021/00007 International Search Report and Written Opinion dated May 25, 2021.

PCT/IB2022/000609 International Invitation to Pay Additional Fees dated Feb. 2, 2023.

PCT/IB2022/000609 International Search Report and Written Opinion dated Apr. 13, 2023.

PCT/IB2022/00343 International Search Report and Written Opinion dated Oct. 28, 2022.

PCT/US2016/01510 International Search Report and Written Opinion dated May 24, 2017.

Post et al. Demodex Folliculorum and Blepharitis Arch. Dermatol. 88(3):298-302 (1963).

PubChem substance SID 381577632 (2019).

Qiao et al. Emerging treatment options for meibomian gland dysfunction. Clinical Ophthalmology 7:1797-1803 (2013).

Rosenkrantz. Practical Applications of Topical Therapy for Allergic, Infectious, and Seborrheic Disorders. Clin. Tech. Small Anim. Pract. 21(3):106-116 (2006).

Rosenthal et al. effect of selenium sulfide on rabbit eyes. South Med J 55:318 (1962).

Schaumberg et al. The International Workshop on Meibomian Gland Dysfunction: Report of the Subcommittee on the Epidemiology Of, and Associated Risk Factors For, MGD. Invest. Ophthalmol. Vis. Sci. 52(4):1994-2005 (2011).

Schieving. The Seven Most Common Grades for Chemicals and Reagents. Nov. 2017 retrieved from https://www,labmanager.com/business-management/the-seven-most-common-grades-for-chemicals-and-reagents-2655.

Seifert et al. Immunocytochemical and ultrastructure evaluation of the distribution of nervous tissue and neuropeptides in meibomian gland. Graefe's Arch Clin Exp Ophthalmol 234:648-656 (1996).

Selenocysteine—American Chemical Society. Available at https://www.acs.org/content/acs/en/molecule-of-the-week/archive/s/selenocysteine.html (Jun. 24, 2019) (Retrieved Jul. 29, 2021).

Selenomethionine_ECHA website. Available at https://echa.europa.eu/information-on-chemicals/cl-inventory-database/-/discli/notification-details/208470/961313 (Retrieved Jul. 29, 2021).

Sengupta et al., Selenoproteins are essential for proper keratinocyte function and skin development. PLoS One 5(8):e12249 (2010).

Siddireddy et al. Predictive Potential of Eyelids and Tear Film in Determining Symptoms in Contact Lens Wearers. Optom Vis Sci 95(11):1035-1045 (2018).

Srinivasan et al. Design of a Precision Medication Dispenser: Preventing Overdose by Increasing Accuracy and Precision of Dosage. IEEE Journal of Translational Engineering in Health and Medicine 6:1-6 (2018) (Art. No. 2800406).

Thygeson et al. Seborrheic blepharitis. Trans Am Ophthalmol Soc. 52:173-88 (1954-1955).

U.S. Appl. No. 14/732,622 Office Action dated Nov. 19, 2015.

U.S. Appl. No. 15/269,833 Office Action dated Aug. 7, 2017.

U.S. Appl. No. 15/269,833 Office Action dated Jan. 11, 2017.

U.S. Appl. No. 15/279,301 Office Action dated Apr. 25, 2019.

U.S. Appl. No. 15/279,301 Office Action dated Aug. 31, 2017.

U.S. Appl. No. 15/279,301 Office Action dated Mar. 14, 2018.

U.S. Appl. No. 15/279,301 Office Action dated Mar. 29, 2017.

(56)          References Cited

OTHER PUBLICATIONS

U.S. Appl. No. 15/279,301 Office Action dated Nov. 27, 2018.
U.S. Appl. No. 16/019,253 Office Action dated May 16, 2019.
U.S. Appl. No. 16/093,615 Office Action dated Dec. 22, 2020.
U.S. Appl. No. 16/093,615 Office Action dated Jul. 6, 2020.
U.S. Appl. No. 16/093,616 Office Action dated Dec. 7, 2020.
U.S. Appl. No. 16/093,616 Office Action dated May 7, 2021.
U.S. Appl. No. 16/093,616 Office Action dated Nov. 23, 2021.
U.S. Appl. No. 16/498,299 Office Action dated Mar. 16, 2022.
U.S. Appl. No. 16/498,299 Office Action dated May 4, 2021.
U.S. Appl. No. 16/498,299 Office Action dated Oct. 9, 2020.
U.S. Appl. No. 16/562,374 Office Action dated Oct. 30, 2019.
U.S. Appl. No. 16/919,749 Office Action dated Oct. 5, 2020.
U.S. Appl. No. 17/171,942 Office Action dated May 25, 2023.
U.S. Appl. No. 17/236,258 Office Action dated Oct. 18, 2022.
U.S. Appl. No. 17/357,749 Office Action dated Nov. 1, 2021.
U.S. Appl. No. 17/471,111 Office Action dated Mar. 31, 2022.
U.S. Appl. No. 17/471,111 Office Action dated Nov. 2, 2021.
U.S. Appl. No. 17/723,090 Office Action dated May 8, 2023.
U.S. Appl. No. 18/119,251 Office Action dated Jul. 6, 2023.
U.S. Appl. No. 16/795,497 Office Action dated Jul. 29, 2021.
Willis et al. Meibomian gland function, lid wiper epitheliopathy, and dry eye symptoms. Investigative Ophthalmology & Visual Science 52(14):3740-3740 (2011).
Wong et al. Selenium (Selsun) in the Treatment of Marginal Blepharitis. AMA Arch Ophthalmol 55(2):246-253 (1956).
Yanagi et al., Subconjunctival administration of bucillamine suppresses choroidal neovascularization in rat. Invest Ophthalmol Vis Sci. 43(11):3495-3499 (2002).
Young et al. Soft contact lens-related dryness with and without clinical signs. Optom. Vis. Sci. 89:1125-32 (2012).
Jackson, Bruce. Blepharitis: current strategies for diagnosis and management. Can J Ophthalmol 43(2):170-179 (2008).
Jagavkar, C. K. Appraisal of Efficacy of Two Anti Dandruff Formulation. Indian Journal of Dermatology, Venereology and Leprology 45(5):336-340 (1979).
Jokl, Danny H-Kauffmann. et al. Bacterial Contamination of Ophthalmic Solutions Used in an Extended Care Facility. British Journal of Ophthalmology 91(10):1308-1310 (2007).
Krauss, Achim H. et al. Improvement of Outcome Measures of Dry Eye by a Novel Integrin Antagonist in the Murine Desiccating Stress Model. Investigative ophthalmology & visual science 56(10):5888-5895 (2015).
Nilforoushan, Mohammad-Reza. et al. Effect of Artificial Tears on Visual Acuity. American Journal of Ophthalmology 140(5):830-835 (2005).
PCT/IB2024/000365 International Search Report and Written Opinion dated Dec. 2, 2024.
PCT/IB2024/000366 International Search Report and Written Opinion dated Dec. 4, 2024.
Post, Charles F, and Einar Juhlin. Demodex Folliculorum and Blepharitis. Archives of Dermatology 88(3):298-302 (1963).
Spectrum. Safety Data Sheet. 1-11 (2018).
U.S. Appl. No. 17/734,900 Office Action dated Nov. 8, 2024.
U.S. Appl. No. 17/855,435 Office Action dated Feb. 26, 2025.
U.S. Appl. No. 17/855,435 Office Action dated Oct. 28, 2024.
U.S. Appl. No. 17/860,886 Office Action dated Feb. 13, 2025.
Barabino et al. Animal Models of Dry Eye: A Critical Assessment of Opportunities and Limitations. Invest. Ophthalmol. Vis. Sci. 45:1641-1646 (2004).
Barabino et al. The Controlled-Environment Chamber: A New Mouse Model of Dry Eye. Invest. Ophthalmol. Vis. Sci. 46:2766-2771 (2005).
Bartlett, Jimmy et al. Loteprednol Etabonate in Ocular Inflammation. US Ophthalmic Review 4(1):57-62 (2011).
Contact Lens Questionnaire-8 (CLDEQ-8). Available at cdn-links. lww.com/permalink/icl/a/icl_2016_04_08_hicksoncurran_15-146_ sdc1.pdf (2016).
Co-pending U.S. Appl. No. 18/759,260, inventors Alster; Yair et al., filed Jun. 28, 2024.
Co-pending U.S. Appl. No. 18/759,278, inventors Alster; Yair et al., filed Jun. 28, 2024.
Craig, Jennifer P. et al. Randomized controlled trial evaluating novel keratolytic for MGD treatment. Poster presented at ARVO. pp. 1-3 (2021).
Di Lemia, V. et al. Profile of tofacitinib citrate and its potential in the treatment of moderate-to-severe chronic plaque psoriasis. Drug Design, Development and Therapy 10:533-539 (2016).
Du, Lin et al. Ruxolitinib Alleviates Uveitis Caused by Salmonella typhimurium Endotoxin. Microorganisms 9(7):1481 (pp. 1-12) (2021).
Dursun et al. A Mouse Model of Keratoconjunctivitis Sicca. Invest. Ophthalmol. Vis. Sci. 43:632-638 (2002).
Falto-Aizpurua, Leyre et al. Emerging treatments in alopecia. Expert opinion on emerging drugs 19(4):545-556 (2014).
Gangaputra, Sapna, et al. Methotrexate for ocular inflammatory diseases. Ophthalmology 116(11):2188-2198 (2009).
Gonzalez, A.J. et al. Oclacitinib (APOQUEL(®)) is a novel Janus kinase inhibitor with activity against cytokines involved in allergy. J Vet Pharmacol Ther 37(4):317-324 (2014).
Huang, JF. Immunomodulatory Effects of Topical Ophthalmic Tofacitinib (Cp-690,550) in Dry Eye Disease. US Ophthalmic Review 7(1):12-15 (2014).
Kennedy Crispin, Milène et al. Safety and efficacy of the JAK inhibitor tofacitinib citrate in patients with alopecia areata. JCI 1(15):e89776 (2016).
Kravetz De Oliviera, Juliana et al., Comparative efficacy of topical oclacitinib 0.1% and tacrolimus 0.01% in canine keratoconjunctivitis sicca. Vet Ophthalmol 22(5):633-643 (2019).
Levy, Lauren L., et al. Treatment of recalcitrant atopic dermatitis with the oral Janus kinase inhibitor tofacitinib citrate. J Am Acad Dermatol 73(3):395-399 (2015).
Mesa, Ruben A. Ruxolitinib, a selective JAK1 and JAK2 inhibitor for the treatment of myeloproliferative neoplasms and psoriasis. IDrugs 13(6):394-403 (2010).
Nichols, Kelly K., et al. The international workshop on meibomian gland dysfunction: executive summary. Invest Ophthalmol Vis Sci 52(4):1922-1929 (2011).
Niederkorn et al. Desiccating Stress Induces T Cell-Mediated Sjögren's Syndrome-like Lacrimal Keratoconjunctivitis. J. Immunol. 176:3950-3957 (2006).
Ocular Surface Disease Index (OSDI) questionaire. Available www. supereyecare.com/resources/OSDI.pdf (2011).
PCT/IB2023/000680 International Search Report and Written Opinion dated May 13, 2024.
PCT/IB2023/000803 International Search Report and Written Opinion dated Jul. 1, 2024.
Pflugfelder et al. A Randomized, Double-Masked, Placebo-Controlled, Multicenter Comparison of Loteprednol Etabonate Ophthalmic Suspension, 0.5%, and Placebo for Treatment of Keratoconjunctivitis Sicca in Patients With Delayed Tear Clearance. Am J Ophthalmol 138:444-57 (2004).
Pflugfelder et al. International Dry Eye WorkShop, 2007. Management and Therapy of Dry Eye Disease: Report of the Management and Therapy Subcommittee of the International Dry Eye WorkShop. Ocul Surf 5:163-178 (2007).
Sadrai, Zahra, et al. PDE4 inhibition suppresses IL-17-associated immunity in dry eye disease. Investigative Ophthalmology & Visual Science 53(7):3584-3591 (2012).
SHA. Ophthalmology. People's Military Medical Press. p. 138 (Apr. 30, 2013).
The Berkeley Dry Eye Flow Chart (DEFC). Available at www. researchgate.net/figure/The-Berkeley-Dry-Eye-Flow-Chart-DEFC-https-doiorg-101371-journalpone0190752g001_fig1_322688369 (2024).
Thode et al. Current and Emerging Therapeutic Strategies for the Treatment of Meibomian Gland Dysfunction (MGD). Drugs 75:1177-1185 (2015).
Thueson, D.O. et al., The roles of pH and concentration in lactic acid-induced stimulation of epidermal turnover. Dermatol Surg. 24(6):641-5 (1998).
US FDA Drug Nomenclature Monograph, No. C-DRG-00201 (Latest revision 2006).
U.S. Appl. No. 17/725,320 Office Action dated Jan. 11, 2024.
U.S. Appl. No. 18/665,222 Office Action dated Jul. 29, 2024.

(56) References Cited

OTHER PUBLICATIONS

U.S. Appl. No. 18/759,260 Office Action dated Sep. 10, 2024.
U.S. Appl. No. 18/759,278 Office Action dated Sep. 9, 2024.
Watson, et al. Efficacy and safety of AZR-MD-001 selenium sulfide ophthalmic ointment in adults with meibomian gland dysfunction: A vehicle-controlled, randomized clinical trial. The Ocular Surface 29:537-546 (2023).
Zhang. Modern Dermatologic Therapeutics. People's Military Medical Press p. 187 (May 31, 2022).
Deardorff. Chapter 86: Ophthalmic Preparations. Remington's Pharmaceutical Sciences (Osol A (Ed). pp. 1498-1517 (1980).
Krassoi et al. Thiorphan enhances bradykinin-induced vascular relaxation in hypoxic/hyperkalaemic porcine coronary artery. Journal of Pharmacy and Pharmacology 55:339-345 (2003).
Stapleton, A Single-center, Vehicle-controlled, Study to Evaluate the Safety, Tolerability, and Pharmacodynamics of AZR-MD001 as Adjunctive Therapy to Conventional Therapeutic Treatment for Meibomian Gland Dysfunction (MGD) or Contact Lens Discomfort (CLD). School of Optometry and Vision Science:1-74 (2020).
U.S. Appl. No. 17/536,986 Office Action dated Mar. 1, 2024.
Cohen et al. Use of selsun in blepharitis marginalis. Am J Ophthalmol 38(4):560-562 (1954).
Lindsley et al. Interventions for chronic blepharitis. Cochran Database Syst Rev 2012(5):CD005556 (2012).

* cited by examiner

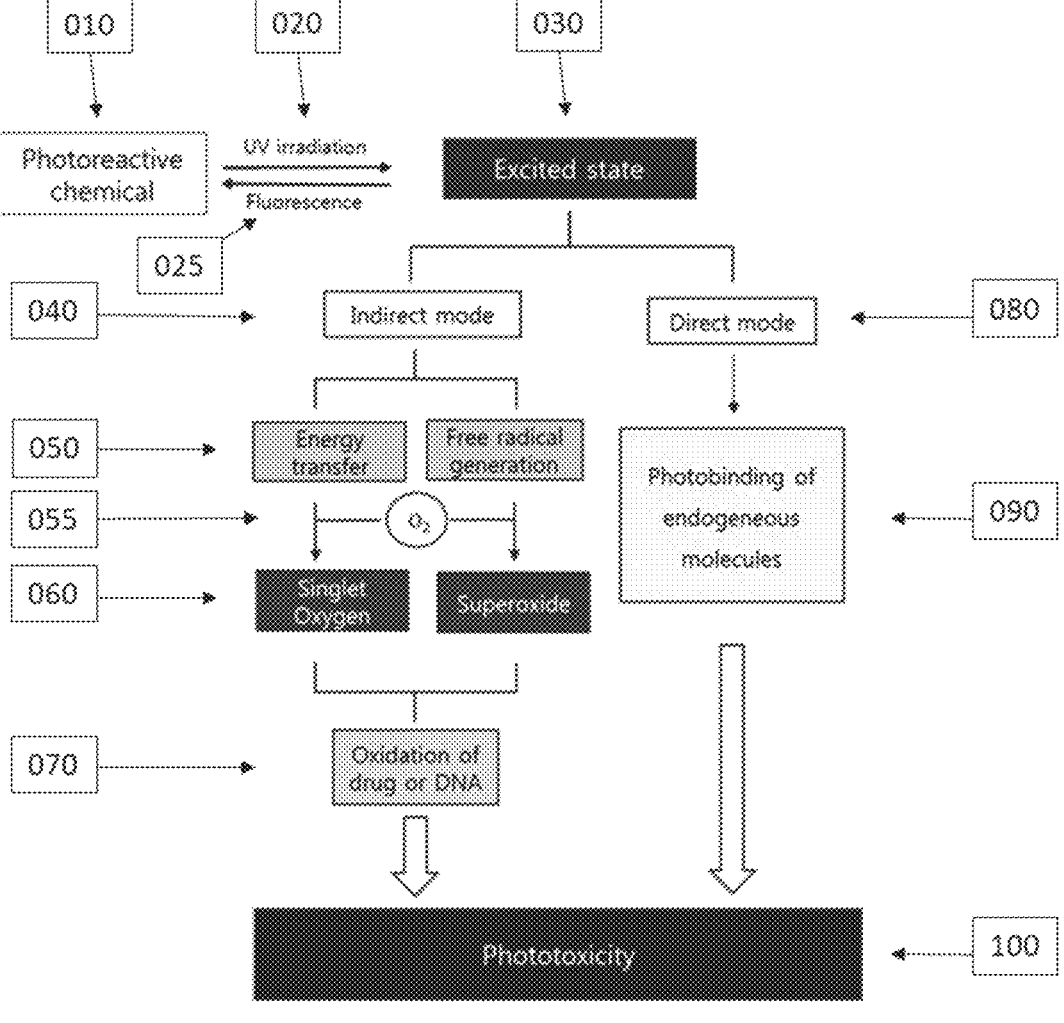

INSTRUCTIONS FOR COMPOSITION AND SENSITIVITY

CROSS-REFERENCE TO RELATED APPLICATIONS

This application is a continuation of U.S. application Ser. No. 17/471,111, filed Sep. 9, 2021 (now U.S. Pat. No. 11,517,586, issued Dec. 6, 2022, which is a continuation of International Application No. PCT/IB2021/000005, filed Jan. 7, 2021, which claims the benefit of U.S. Provisional Application No. 62/959,738 filed Jan. 10, 2020, each of which is hereby incorporated by reference in its entirety.

BACKGROUND OF THE INVENTION

Selenium sulfide ($SeS_2$) is indicated for the treatment of dermatological condition such as seborrheic dermatitis, tinea versicolor and dandruff. It is typically used as shampoo, foam or lotion at commercially available concentrations of 1% and 2.5% and is applied for several minutes, then rinsed off. The use of $SeS_2$ can be associated with known side effects that are listed in the drug insert and which may include irritation, burning, and on rare occasion, loss and discoloration of hair. Contact of a significant amount of preparations containing high-concentration selenium sulfide with mucous membranes of the eye may cause irritation (e.g., stinging) and prolonged contact (e.g., overnight application) of preparations containing $SeS_2$ with the skin may cause local irritation.

Adverse events reported following topical ocular use of selenium sulfide containing products include: superficial punctate keratitis and conjunctivitis which resolved upon cessation of treatment. When $SeS_2$ is applied topically for the treatment of tinea versicolor, skin irritation may occur in the genital areas and/or folds of the skin. $SeS_2$ lotions can also cause rebound oiliness of the scalp. *AHFS Drug Information* 2010.

Discoloration of various shades of natural and dyed hair has occurred following topical application of $SeS_2$ lotion. Hair discoloration is uncommon and is usually associated with poor or no rinsing following shampooing with the $SeS_2$ lotion. The manufacturers state that hair discoloration can be minimized by careful rinsing of the hair after treatment with the drug. Shampooing with a 2.5% lotion of the drug has also reportedly caused diffuse hair loss, which resolved 1-2 weeks following discontinuance of the drug.

$SeS_2$ lotion has been reported to cause systemic toxicity following topical application to damaged skin. Following long-term topical use of the lotion in a woman with an open lesion on her scalp, systemic signs and symptoms of toxicity including tremors, severe perspiration, garlicky breath, pain in the lower abdomen, weakness, lethargy, loss of appetite, and occasional vomiting occurred. Signs and symptoms of toxicity resolved within 10 days after discontinuing the drug. Selenium may be toxic when taken by mouth in high doses (>400 μg per day) or for long durations. Acute selenium poisoning is potentially lethal due to cardiocirculatory failure and/or pulmonary edema. Gastrointestinal effects are generally the first symptoms seen with acute selenium poisoning. Acute effects may include: vomiting, hypersalivation, diarrhea, abdominal pain, a burning sensation in the nostrils and/or oral mucosa, chemical burns of the alimentary tract and a garlic-like odor on the breath. Poisoning from long-term use is similar to arsenic poisoning, with symptoms including hair loss, white horizontal streaking on fingernails, nail inflammation, fatigue, irritability, nausea, vomiting, garlic breath odor, and a metallic taste. Selenium can also cause muscle tenderness, tremor, light-headedness, facial flushing, blood clotting problems, liver and kidney problems, and other side effects. Acute systemic effects of selenium are not expected in the target patient population with the proposed dosing regimen.

Non-specific allergic reactions, including rash and urticaria, have been reported rarely. Selenium compounds have UV protective effects. Specifically, topical selenium compounds increase the minimum dose of UV radiation required to cause skin reddening and protect against skin damage caused by UVB exposure (radiation with a wavelength of about 290 nm to about 320 nm). In some instances, this is because intracellularly selenium's major function is upregulation of the enzyme glutathione peroxidase (GPX) as an antioxidant.

In the 1950s and early 1960s, several investigators attempted to use ophthalmic preparation of $SeS_2$ to treat seborrheic blepharitis, typically associated with scaling at the eyelid margin and which affects many of those patients suffering from seborrheic dermatitis. These clinicians treated hundreds of patients over a course of time ranging between 1 month and 1 year using different methods including in-office application, home application, daily application, or application on alternating days.

Cohen and others using ophthalmic preparation of $SeS_2$ in patients first investigated the ophthalmic preparation in animals in order to determine what would be a safe concentration for the use in humans; they concluded that 0.5% is safe. In the reports describing their experience, most investigators concluded that the $SeS_2$ 0.5% was effective in treating seborrheic blepharitis and reported side effects primarily focusing on keratitis. Keratitis is an inflammatory response in the cornea typically causing significant pain and damage to the superficial epithelial cells which can be identified using corneal fluorescein staining.

Different means of application were described by the investigators including from careful application in the office with rinsing of excess material as well as at-home application with complete rinsing after a short period. It was clearly stated that careful application and rinsing were important to avoid harmful effects. It was further understood that patients who developed severe reactions were improperly applying the treatment to the eye or failed to observe thorough rinsing procedures.

Lavyel 1960, described the use of Selsunef® ointment, a 0.5% $SeS_2$ ointment produced by Abbott. Selsunef® was used in the clinic in 80 subjects, where gentle and controlled application was performed by a physician who also removed the ointment after 30 min by a swab of cotton wool. Great care was always taken not to introduce any of the ointment into the conjunctival sac. In one case, where the patient administered Selsunef® to himself, contrary to medical advice, a rather severe keratitis promptly developed.

SUMMARY

Another ophthalmic condition related to blepharitis, meibomian gland dysfunction (MGD), is a common disease, in which a patient's meibomian glands produce insufficient meibum that would otherwise prevent dryness of the eye. Meibum is an oily substance comprised largely of lipids that helps maintain the eye's tear film by preventing evaporation or pooling. In MGD, obstruction of the meibomian glands prevents the secretion of meibum, therefore causing dry eyes, pain, and blepharitis in many patients. In order to alleviate the obstruction of the meibomian glands and restore lipid production (e.g., meibum production), ophthalmic preparations of $SeS_2$ may be applied to the eyelid, eyelid margin, ocular surface, or surrounding tissues. Described herein are the methods of use for an ophthalmic preparation containing $SeS_2$, particularly wherein side effects, such as ocular keratitis are reduced or eliminated. In some instances, administration can be administered by a patient at home (e.g., chronically) (e.g., on a daily basis or less frequently, if appropriate) on the eyelid or over the eyelid margin.

Adverse effects (e.g., pain, local irritation, inflammation, redness, keratosis, etc.) have been identified in applications of $SeS_2$ in or around the eye, particularly when high concentrations of $SeS_2$ are utilized. In certain instances, administration of therapeutically effective concentrations of $SeS_2$ (e.g., to the eyelid margin) have been found to minimize adverse effects, while also providing therapeutic benefit. It has further been found that reducing exposure to light (e.g., UV light) following administration of the selenium disulfide compositions further reduces the incidents of side effects in ophthalmic applications (e.g., in methods involving administration to the lid margin of an individual).

In certain embodiments provided herein are methods of treating a disease or disorder in or around the eye in an individual in need thereof. In some embodiments, the method comprises administering a therapeutically effective amount of a pharmaceutical composition to an ocular surface, surrounding ocular tissues, eyelid, eyelid margin, or a combination thereof of the individual. In certain embodiments, the pharmaceutical composition comprising a therapeutically effective amount of selenium disulfide ($SeS_2$) to the individual, such as to the eyelid margin of the individual in need thereof. In some embodiments, the individual limits, avoids, or is instructed to limit or avoid (e.g., via oral communication and/or written instruction) exposure to light (e.g., at least to the location to which the composition was administered, to the eye or eyes, or the like) following administration.

In some embodiments, limiting or avoiding exposure to light following administration of the composition reduces (e.g., the incidences of and/or rate of) keratitis (e.g., relative to administration that does not limit or avoid exposure to light), such as in or around the eye. In some instances, the keratitis is associated with photosensitivity. In some embodiments, exposure to light is limited or avoided for any suitable time, such as for at least 30 minutes. In some embodiments, exposure to light is limited or avoided for at least 60 minutes. In some embodiments, exposure to light is limited or avoided for at least 2 hours. In some instances, increased concentrations and/or amounts of selenium disulfide in the composition result in increased rates of and/or incidences of keratitis or other adverse effect. As such, in certain embodiments, light is avoided for longer periods of time than when compositions with lower concentrations and/or amounts of active are administered.

In some embodiments, the composition is administered to the lid margin of the individual. In certain embodiments, administration of the composition to the ophthalmic surface is avoided. In some embodiments, while light may be avoided following administration, the composition is administered under good-light conditions, such as to avoid unwanted administration of the composition to the surface of the eye.

In some embodiments, for a period of time following administration of the composition, the site to which the composition was administered is generally maintained or the individual is instructed to maintain the site to which the composition was administered in low-light conditions. In some embodiments, the low-light conditions are about 100 lux or less, about 50 lux or less, or about 25 lux or less.

In some embodiments, for a period of time following administration of the composition, the site to which the composition was administered is generally not exposed to or the individual is instructed to limit or avoid exposure of the site to which the composition was administered to high-light conditions. In some embodiments, the high-light conditions are about 100 lux or more, about 500 lux or more, or about 1,000 lux or more.

In some embodiments, the individual limits, avoids, or is instructed in a manner such as to limit or avoid exposure to light following administration by administering or being instructed to administer the composition at a specific time of day. In some embodiments, the specific time of day is about later than about hour before dusk. In some embodiments, the specific time of day is after dusk (nighttime). In some embodiments, the specific time of day is before (e.g., within an hour, half-hour, or the like of) bedtime.

In some embodiments, the individual limits, avoids, or is instructed in a manner such as to limit or avoid exposure (e.g., of the location to which the composition was administered, to the eye or eyes, or the like) to light following administration by at least partially obstructing or being instructed to obstruct (e.g., direct) some or all light (e.g., sunlight) to the site to which the composition was administered during and/or following administration. In some embodiments, obstruction of light is achieved by wearing headwear and/or eyewear that at least partially obstructs light. In some embodiments, the headwear is a hat. In some embodiments, the eyewear is sunglasses or goggles.

In some embodiments, the individual self-administers the composition.

In some embodiments, limiting exposure to light comprises limiting exposure to at least some wavelengths of light. In some embodiments, limiting exposure to light comprises limiting exposure to ultraviolet (UV) light. In some embodiments, limiting exposure to light comprises limiting exposure to sunlight. In some embodiments, the individual is instructed to remain indoors. In some embodiments, the individual avoids is instructed to avoid sunlight or ultraviolet (UV) light (e.g., at least where the composition is administered).

In some embodiments, the disease or disorder in or around the eye is meibomian gland dysfunction (MGD), blepharitis, seborrheic blepharitis, Demodex infestation, dry eye syndrome, hyperkeratosis, dermatitis, keratitis, contact lens discomfort, lid wiper epitheliopathy (LWE), Keratoconjunctivitis Sicca, Sjogren's Syndrome, or ocular rosacea. In some embodiments, the disease or disorder in or around the eye is Blepharitis or Seborrheic Blepharitis.

In some embodiments, the composition comprises $SeS_2$ in a therapeutically effective concentration. In some embodiments, the therapeutically effective concentration is about 0.1 wt. % to about 10 wt. % (e.g., about 0.1 wt. % to about 10 wt. %, or about 0.5 wt. % to about 1 wt. %). In some embodiments, the composition is administered in a volume of less than 25 μL. In some embodiments, the composition is administered in a volume of about 1 μL to about 20 μL (e.g., about 2 μL to about 15 μL, or about 3 μL to about 10 μL).

In some embodiments, the composition or formulation is a semi-solid (e.g., gels, cream, paste), strip, emulsion, suspension, foam, lotion, spray, patch, implant (e.g., slow release, biodegradable, semi-degradable, or non-degradable), lipid base systems (e.g., solid lipid nano/micro particles, liposomes, exosome, micelles, micro/nano emulsions, cubosomes, cochleatses, niosomes, lipospheres), silica based system (e.g., mesoporous), polymer based system, nano and/or micro-spheres, nano- and/or micro-capsules, nano- and/or micro-particles, or the like. In some embodiments, the semi-solid is an ointment. In some embodiments, (i) the composition is administered in a sufficiently low volume, and (ii) following administration, exposure to light of the site to which the composition was administered is sufficiently low, such that keratitis (e.g., of an ocular surface of the individual) is reduced or avoided. In some embodiments, lower concentration can support more light exposure with minimal risk of phototoxicity. In some embodiments, the amount of light exposure tolerated and duration to avoid light exposure is correlated to the dose and concentration of $SeS_2$ administered.

Certain embodiments provided herein are methods for treating a disease or disorder in or around the eye in an individual in need thereof, such process comprising protecting an ocular surface of the individual with a barrier. In specific embodiments, the process further comprises administering a therapeutically effective amount of a pharmaceutical composition to the ocular surface of the individual. In specific embodiments, the pharmaceutical composition comprises a therapeutically effective amount of selenium disulfide ($SeS_2$). In some embodiments, protecting of the ocular surface of the individual comprises administering an ointment or hyaluronic acid (HA) to the ocular surface (e.g., thereby forming the barrier by interacting hyaluronic acid (HA) with mucin on the ocular surface). In some embodiments, the hyaluronic acid (HA) has a molecular weight of at least 900 kDa. In some embodiments, the barrier is a contact lens.

In some embodiments, the protecting the ocular surface comprises administering an additive molecule to the ocular surface (e.g., prior to administration of a pharmaceutical composition and/or concurrently therewith), the additive molecule comprising a molecule configured to capture a free radical or photosensitized $SeS_2$. In some embodiments, the free radical is a reactive oxygen species (ROS). In some embodiments, the additive comprises a phenolic compound, vitamin E, vitamin C, carotenes, ferritin, ceruloplasmin, selenium, reduced glutathione (GSH), manganese, ubiquinone, zinc, flavonoids, coenzyme Q, melatonin, bilirubin, taurine, or cysteine.

In some embodiments, the barrier prevents the $SeS_2$ from contacting the ocular surface.

In some embodiments, administering a therapeutically effective amount of pharmaceutical composition to the ocular surface, surrounding ocular tissues, or a combination thereof of the individual comprises applying the pharmaceutical composition with a finger. The finger can be a finger of the individual.

While selenium containing shampoos have broad commercial use, adverse effects are not or are rarely observed. It is surprising that in ophthalmic applications, such as described herein, that adverse effects, such as photosensitivity, are prevalent. In some instances, such prevalence in adverse effects results from increased duration of exposure (e.g., short for shampoo), different exposure location (e.g., topical/scalp vs. eye), different formulation (e.g., shampoo vs. the formulations described herein), or a combination of such differences. In specific embodiments, provided herein are compositions and methods of administering compositions, wherein the composition is not a shampoo.

Additional aspects and advantages of the present disclosure will become readily apparent to those skilled in this art from the following detailed description, such that only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1 illustrates a flowchart depicting mechanisms by which light may interact with a photosensitive chemical to produce phototoxicity in an individual in contact with said photosensitive chemical.

DETAILED DESCRIPTION

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of" The phrase "consisting essentially of" is used herein to require the specified feature(s) as well as those which do not materially affect the character or function of the claimed disclosure. As used herein, the term "consisting" is used to indicate the presence of the recited feature alone.

Provided in certain embodiments herein are methods for treating a disease or disorder in or around the eye in an individual with a therapeutically effective amount of a pharmaceutical composition. In specific embodiments, the composition comprises selenium disulfide ($SeS_2$). In some embodiments, the individual limits, avoids, or is instructed in a manner such as to limit or avoid exposure to light following administration. As discussed herein, in some instances, exposure of the treated area to light, especially sunlight or other ultraviolet light sources, in order to prevent, reduce, or limit the risk of, the rate of, and/or incidences of a side effect, such as keratitis. In some instances, prevention, reduction or limitation of the side effect of $SeS_2$ is greater and/or more likely when the $SeS_2$ composition has high concentration of $SeS_2$ and/or the $SeS_2$ composition is provided in a high dose.

In certain embodiments, the disease or disorder in or around the eye is a disease or condition treated or treatable by a composition, such as described herein. In some embodiments, the disease or disorder may be one or more conditions selected from the group comprising meibomian gland dysfunction (MGD), blepharitis, seborrheic blepharitis, Demodex infestation, dry eye syndrome, hyperkeratosis, dermatitis, keratitis, contact lens discomfort, lid wiper epitheliopathy (LWE), Keratoconjunctivitis Sicca, Sjogren's Syndrome, or ocular rosacea. In some embodiments, the disease or disorder in or around the eye is meibomian gland dysfunction (MGD). In some embodiments, the disease or disorder in or around the eye is blepharitis. In some embodiments, the disease or disorder in or around the eye is seborrheic blepharitis. In some embodiments, the disease or disorder in or around the eye is blepharitis associated with MGD. In some embodiments, the disease or disorder in or around the eye is dry eye syndrome. In some embodiments, the disease or disorder in or around the eye is a condition characterized by insufficient secretion of lipids.

In certain embodiments, light avoided according to any method provided herein is a light that may result in phototoxicity and/or other adverse effect when combined with a therapeutic administration of a composition provided herein in or around the eye. In specific embodiments, all wavelength of light are partially or completely blocked. In other embodiments, select wavelengths of light are partially or completely blocked. In some embodiments, the light includes infrared light, visible light, ultraviolet light, certain wavelengths thereof, and/or combination thereof. In specific embodiments, light comprises visible and/or ultraviolet light. In some embodiments, the light comprises visible light. In some embodiments, the light comprises ultraviolet light. In some embodiment, the ultraviolet light comprises both UVA and UVB light. In some embodiments, light comprises UVA or UVB light. In some embodiments, light is from the sun (sunlight). In some embodiments, light is not sunlight.

In certain embodiments, methods provided herein provide for therapies involving reduced (e.g., incidence or rates) or eliminated photosensitive reaction (e.g., adverse effects resulting from a combination of light and therapeutic administration of a composition provided herein) or photosensitivity (which descriptions are used interchangeably herein). In some instances, such adverse effects refer to an adverse physiological response, such as, by way of non-limiting example, keratitis, inflammation, pain, irritation, flaking, redness, discoloration, or any combination thereof. In some instances, such adverse effects refer to a feeling of grittiness, a feeling of a foreign body in the eye of an individual, blurry vision, redness, tired eyes, symptoms of dry eye disorder, stinging, watery eyes, irritation, lid abnormalities, corneal abrasion, keratitis, photophobia, staining, or any combination thereof. A photoreactive chemical can cause photosensitivity in an individual in contact with said photoreactive chemical through a direct or indirect mechanism as described in FIG. 1. Photosensitivity comprises phototoxicity and photoallergic effects.

FIG. 1 illustrates a non-limiting schematic of an exemplary mechanism by which a photoreactive chemical 010 may induce phototoxicity 100 in an individual are illustrated. When ultraviolet (UV) radiation 020 or any other sufficiently energetic photon interacts with a photoreactive chemical 010, said photoreactive chemical 010 is elevated to an excited state 030, such that energy from the photon is imparted upon the photoreactive chemical 010. The excited state 030 species can expel energy in the form of fluorescence 025 or can impart energy upon a second molecule as further described by the indirect mode 040 or direct mode 080.

The indirect mode of phototoxicity 040 is facilitated by oxygen 055, such that the excited state 030 species can impart energy upon oxygen 055 via energy transfer or free radical generation 050. Both energy transfer and free radical generation 050 to oxygen 055 generates what is called a reactive oxygen species (ROS), illustrated in FIG. 1 by two common species, singlet oxygen and superoxide 060. An ROS such as 060 is highly reactive and can cause oxidation of a variety of molecules which may include a drug or DNA 070 among others. Following oxidation, the newly transformed molecule 070 can exert physiological effects in an individual in contact with the photoreactive chemical 010. In specific embodiments, the photoreactive chemical 010 enhances the inherently damaging (e.g., oxidizing) properties of UV radiation 020 by catalyzing the formation of ROS 060 at a location in contact with the photoreactive chemical 010. Thus, preventing UV radiation or other sufficiently energetic photons from interacting with a photoreactive chemical 010 may provide protection from phototoxicity 100 and associated photosensitivity.

The direct mode of phototoxicity 080 is independent of oxygen. In the direct mode 080, the excited state 030 species described herein can interact with (e.g., photobinding of) endogenous molecules 090 including but not limited to small molecules, peptides, proteins, and nucleic acids. Photobinding of endogenous molecules 090 can directly exert phototoxicity 100 in a manner similar to that previously described.

In some embodiments, to avoid the possibility of $SeS_2$ interacting with light, patients are instructed to avoid exposure of their ocular surface and surrounding tissues to light following application. The time during which to avoid light maybe determined based on the dose and concentration applied. Means for avoiding light exposure may comprise the following: (1) bedtime application after which the subject stays in bed with no light exposure, (2) daytime application such that the individual stays in a dim or dark environment following treatment, and (3) wearing protective headwear or eyewear to shield the treated area from light (e.g., dark sunglasses or UV protective sunglasses).

In some embodiments, the pharmaceutical composition comprises $SeS_2$ in a therapeutically effective concentration. In some embodiments, the pharmaceutical composition comprises $SeS_2$ in less than a therapeutically effective concentration. In some embodiments, the pharmaceutical composition comprises $SeS_2$ in a homeopathic concentration. In some embodiments, the pharmaceutical composition comprises $SeS_2$ in greater than a therapeutically effective concentration.

In some embodiments, the therapeutically effective concentration is about 0.1 wt. % to about 2.5 wt. % (e.g., about 0.5 wt. % to about 1 wt. %). In some embodiments, the therapeutically effective concentration comprises at least about 0.01 wt. %, about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1.0 wt. %, about 1.25 wt. %, about 1.5 wt. %, about 1.75 wt. %, about 2.0 wt. %, about 2.5 wt. %, about 3.0 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, about 9.5 wt. %, about 10.0 wt. %, about 10.5 wt. %, about 11.0 wt. %, about 11.5 wt. %, about 12.0 wt. %, about 15.0 wt. % or more of selenium disulfide ($SeS_2$). In some embodiments, the therapeutically effective concentration comprises at most about 11.0 wt. %, about 10.0 wt. %, about 9.0 wt. %, about 8.0 wt. %, about 7.0 wt. %, about 6.0 wt. %, about 5.0 wt. %, about 4.0 wt. %, about 3.0 wt. %, about 2.5 wt. %, about 2.0 wt. %, about 1.75 wt. %, about 1.5 wt. %, about 1.25 wt. %, about 1.0 wt. %, about 0.95 wt. %, about 0.9 wt. %, about 0.85 wt. %, about 0.8 wt. %, about 0.75 wt. %, about 0.70 wt. %, about 0.65 wt. %, about 0.60 wt. %, about 0.55 wt. %, about 0.5 wt. %, about 0.45 wt. %, about 0.4 wt. %, about 0.35 wt. %, about 0.3 wt. %, about 0.25 wt. %, or less. In some embodiments, the therapeutically effective concentration comprises about 0.01 wt. % to about 15.0 wt. %, 0.01 wt. % to about 10.0 wt. %, 0.01 wt. % to about 9.0 wt. %, 0.01 wt. % to about 8.0 wt. %, 0.01 wt. % to about 7.0 wt. %, 0.01 wt. % to about 6.0 wt. %, 0.01 wt. % to about 5.0 wt. %, 0.01 wt. % to about 4.0 wt. %, about 0.01 wt. % to about 3.0 wt. %, about 0.01 wt. % to about 2.0 wt. %, about 0.01 wt. % to about 1.5 wt. %, about 0.01 wt. % to about 1.0 wt. %, about 0.01 wt. % to about 0.5 wt. %, about 0.01 wt. % to about 0.1 wt. %, about 0.01 wt. % to about 0.05 wt. %, about 0.05 wt. % to about 4.0 wt. %, about 0.05 wt. % to about 3.0 wt. %, about 0.05 wt. % to about 2.0 wt. %, about 0.05 wt. % to about 1.5 wt. %, about 0.05 wt. % to about 1.0 wt. %, about 0.05 wt. % to about 0.5 wt. %, about 0.05 wt. % to about 0.1 wt. %, about 0.1 wt. % to about 4.0 wt. %, about 0.1 wt. % to about 3.0 wt. %, about 0.1 wt. % to about 2.0 wt. %, about 0.1 wt. % to about 1.5 wt. %, about 0.1 wt. % to about 1.0 wt. %, about 0.1 wt. % to about 0.5 wt. %, about 0.5 wt. % to about 4.0 wt. %, about 0.5 wt. % to about 3.0 wt. %, about 0.5 wt. % to about 2.0 wt. %, about 0.5 wt. % to about 1.5 wt. %, about 0.5 wt. % to about 1.0 wt. %, about 1.0 wt. % to about 4.0 wt. %, about 1.0 wt. % to about 3.0 wt. %, about 1.0 wt. % to about 2.5 wt. %, about 1.0 wt. % to about 2.0 wt. %, about 1.0 wt. % to about 1.5 wt. %, or any combination thereof. In some instances, administration or use of lower concentrations of $SeS_2$ (e.g., 0.5 wt. %) results in fewer adverse effects. In some instances, administration or use of lower concentrations of $SeS_2$ (e.g., 0.5 wt. %) results in fewer adverse effects when light is avoided after administration, such as administration in the evening or at night.

In some embodiments, the pharmaceutical composition is administered in a volume of less than 25 μL. In some embodiments, the pharmaceutical composition is administered in a volume of about 1 μL to about 20 μL (e.g., about 2 μL to about 15 μL, or about 3 μL to about 10 μL). In some embodiments, the volume of the pharmaceutical composition or the volume of pharmaceutical composition administered using a method provided herein (e.g. using a swab or a finger) is at most about 30 μL, at most about 25 μL, at most about 20 μL, at most about 15 μL, at most about 10 μL, or at most about 5 μL. In some embodiments, the volume is at least about 0.01 microliters (μL), at least about 0.05 μL, at least about 0.1 μL, at least about 0.5 μL, at least about 1 μL, at least about 5 μL, at least about 10 μL, at least about 15 μL, at least about 20 μL, or more. In some embodiments, the volume is from about 0.01 μL to about 50 μL, about 0.1 μL to about 30 μL, about 0.5 μL to 25 μL, about 1 μL to 25 μL, about 10 μL to 25 μL, or about 2.5 μL to about 10 μL.

In some embodiments, the therapeutically effective amount of $SeS_2$ is at least about 0.1 milligrams (mg), at least about 0.2 mg, at least about 0.3 mg, at least about 0.5 mg, at least about 1 mg, at least about 2 mg, at least about 2.5 mg, or the like. In some embodiments, the therapeutically effective amount of selenium disulfide ($SeS_2$) is about 25 mg or less, about 15 mg or less, about 10 mg or less, 7.5 mg or less, about 5 mg or less. In some embodiments, the therapeutically effective amount of $SeS_2$ is about 0.5 mg, about 1 mg, about 2 mg, about 3 mg, about 4 mg, about 5 mg, about 6 mg, about 8 mg, about 10 mg, or the like. In some embodiments, the therapeutically effective amount of $SeS_2$ is about 4 mg.

In some embodiments, the composition is a semi-solid. In some embodiments, the composition is an ointment. In some embodiments the composition is applied using a finger. In some embodiments the composition is applied using a swab.

In some embodiments, the pharmaceutical composition is applied to the ocular surface, surrounding ocular tissues, eyelid, eyelid margin, lid wiper, meibomian gland, mucocutaneous margin, eyelashes, lash line, lash follicle, tarsal glands, palpebral border, medial angle, lacrimal papilla and punctum, dermal or epidermal tissue within 1 cm of the ocular surface, dermal or epidermal tissue within 2 cm of the ocular surface, or any combination thereof.

In some instances, the composition is self-administered. The composition can be administered via a swab or finger. Alternatively and/or additionally, the composition is administered to the individual by a medical practitioners (e.g., a doctor, a nurse, a skilled medical technician, etc.). Alternatively and/or additionally, the composition is administered to the individual by another individual or by a machine. In some embodiments, finger administration is preferred. In some instances, administration of a composition provided herein with a finger, rather than with, e.g., a swab, results in improved therapeutic efficacy.

In some instances, the composition is administered under good-light condition (e.g., under sunlight, under a light having at least 50 lux or more, at least 100 lux or more, about 500 lux or more, or about 1,000 lux or more. In some instances, limiting or avoiding exposure to light following administration of the composition reduces keratitis associated with photosensitivity, at least 10%, at least 20%, at least 30%, at least 40%, at least 50%, at least 60%, at least 70%, at least 80%, at least 80%, at least 90%, compared to or relative to administration that does not limit or avoid exposure to light (e.g., either same individual with or without light exposure, or different individuals having similar conditions with or without light exposure, etc.).

The duration of limiting or avoiding exposure to light may vary depending on the condition of the individual, dose of the composition, concentration of the $SeS_2$ in the composition, previous treatment history of the individual, etc. In some instances, the exposure to light is limited or avoided for at least 30 minutes, at least 60 minutes, at least 90 minutes, at least 120 minutes, at least 3 hours, at least 6 hours, etc.

The amount of light that is permitted or prevented (e.g., limited, avoided, or instructed to do so, etc.) after the administration of the composition may also vary depending on the condition of the individual, dose of the composition, concentration of the $SeS_2$ in the composition, previous treatment history of the individual, etc. In some instances, an individual is limited, avoided, or instructed to do limit or avoid any high lights (e.g., about 100 lux or more, about 500 lux or more, or about 1,000 lux or more.). In some instances, an individual is allowed to be exposed or the site to which the composition was administered is exposed or maintained at low-light conditions (e.g., about 100 lux or less, about 50 lux or less, or about 25 lux or less, etc.). In some embodiments, for a period of time following administration of the compound, the site to which the composition was administered is generally maintained or the individual is instructed to maintain the site to which the composition was administered in low-light conditions as described herein. In some embodiments, the individual maintains the site to which the composition was administered in low-light conditions. In some embodiments, the individual reads printed instructions to maintain the site to which the composition was administered in low-light conditions. In some embodiments, the individual is provided printed instructions to maintain the site to which the composition was administered in low-light conditions. In some embodiments, the individual is provided auditory instructions to maintain the site to which the composition was administered in low-light conditions. In some embodiments, the individual is provided non-auditory instructions to maintain the site to which the composition was administered in low-light conditions.

In some embodiments, low-light conditions are characterized by the physiological response in an observer of said light conditions. In some embodiments, low-light conditions are characterized in relation to wavelength, lux (lumens/m$^2$), or the combination thereof. In some embodiments, low-light conditions are provided by night. In some embodiments, low-light conditions are provided by obstruction of the sun. In some embodiments, low-light conditions are provided by being indoors. In some embodiments, low-light conditions are provided by naturally occurring conditions (e.g., overcast weather). In some embodiments, low-light conditions are provided by exclusion of specific wavelengths or ranges of wavelengths of light. In some embodiments, low-light conditions are provided by a darkroom. In some embodiments, low-light conditions are provided by use of a safelight In some embodiments, low-light conditions are at most about 1000 lux, about 250 lux, about 100 lux, about 50 lux, about 25 lux, about 10 lux, about 1 lux, about 0.1 lux, about 0.01 lux, about 0.001 lux or less. In some embodiments, low-light conditions are at least about 0.001 lux, about 0.01 lux, about 0.1 lux, about 1 lux, about 10 lux, about 25 lux, about 50 lux, about 100 lux, about 250 lux, about 1000 lux, or more. In some embodiments, low-light conditions are between about 0.001 to about 1000 lux, about 0.001 to about 250 lux, about 0.001 to about 100 lux, about 0.01 to about 1000 lux, about 0.01 to about 250 lux, about 0.01 to about 100 lux, about 0.1 to about 1000 lux, about 0.1 to about 250 lux, about 0.1 to about 100 lux, about 1 to about 1000 lux, about 1 to about 200 lux, about 1 to about 100 lux, about 10 to about 1000 lux, about 10 to about 200 lux, about 10 to about 100 lux, about 25 to about 1000 lux, about 25 to about 250 lux, about 25 to about 100 lux, about 50 to about 1000 lux, about 50 to about 250 lux, or about 50 to about 100 lux.

In some embodiments, the individual limits, avoids, or is instructed in a manner such as to limit or avoid exposure to light following administration by at least partially obstructing or being instructed to obstruct (e.g., direct or indirect) some or all light from one or more, or any light sources (e.g., sunlight) to the site to which the composition was administered during and/or following administration. In some embodiments, the individual limits, avoids, or is instructed in a manner such as to limit or avoid exposure to light following administration by at least partially obstructing or being instructed to obstruct some or all light to the site to which the composition was administered as well as the surrounding tissues during and/or following administration.

In some embodiments, the individual directs or is instructed to direct light following administration and limiting/avoiding lights after administration by at least partially directing or being instructed to direct some or all light (e.g., sunlight) to the site to which the composition was administered.

In some embodiments, the individual limits, avoids, or is instructed in a manner such as to limit or avoid exposure to light following administration by administering or being instructed to administer the composition at a specific time of day. In some embodiments, the specific time of day is later than about an hour before dusk. In some embodiments, the specific time of day is later than about two hours before dusk. In some embodiments, the specific time of day is later than about dusk. In some embodiments, the specific time of day is later than about an hour after dusk. In some embodiments, the specific time of day is later than about two hours after dusk. In some embodiments, the specific time of day is after dusk (nighttime). In some embodiments, the specific time of day is more than about an hour before bedtime. In some embodiments, the specific time of day is less than about an hour before bedtime. In some embodiments, the specific time of day is less than about 30 minutes before bedtime. In some embodiments, administration is performed at night. In specific embodiments, night time administration is a time after 4:00 PM, after 5:00 PM, after 6:00 PM, or the like.

In some embodiments, obstruction of light is achieved by wearing headwear and/or eyewear that at least partially obstructs light. In some embodiments, obstruction of light is achieved by wearing a headwear and/or an eyewear that entirely obstructs light. In some embodiments, obstruction of light is achieved by wearing a headwear and/or an eyewear that at least partially obstructs specific wavelengths of light. In some embodiments, the light obstructed by a headwear and/or an eyewear is not visible light. In some embodiments, the light obstructed by a headwear and/or an eyewear comprises both visible light as well as other forms of radiation. In some embodiments, obstruction of light is achieved by wearing a headwear and/or an eyewear that at least partially obstructs ultraviolet radiation, visible light, infrared radiation, x-rays, and/or gamma rays.

In some embodiments, the headwear is a hat. In some embodiments, the headwear is a hat with a bill or a brim. In some embodiments, the headwear is a hat without a bill or a brim.

In some embodiments, the eyewear is sunglasses or goggles. In some embodiments, the eyewear is a contact lens. In some embodiments, the eyewear comprises one or more lens. In some embodiments, the eyewear comprises one or more polarized lens. In some embodiments, the eyewear comprises one or more reflective lens. In some embodiments, the eyewear comprises one or more shaded lens. In some embodiments, the eyewear is blindfold. In some embodiments, the eyewear comprises natural or synthetic fibers or a combination thereof. In some embodiments, the eyewear comprises a reflective surface. In some embodiments, the eyewear comprises a lens or mirror. In some embodiments, the eyewear comprises fabric, a polymer, a plastic, a metal, a non-metal, plant material, plant-derived material, synthetic material, or any combination thereof.

In some embodiments, reduced or avoidance of keratitis is achieved by combining two conditions: i) administering the composition in a sufficiently low volume (even with high concentration), and ii) following administration, exposure to light of the site to which the composition was administered is sufficiently low. In some instances, a lower concentration of $SeS_2$ can support more light exposure with minimal or reduced risk of phototoxicity. In some embodiments, the amount of light exposure tolerated and duration to avoid light exposure is at least partially correlated to the dose and/or concentration of $SeS_2$ composition administered.

In some embodiments, the adverse effect of $SeS_2$ interacting with light is prevented or reduced by protecting the ocular surface of an individual with a barrier. In specific embodiments, the process further comprises administering a therapeutically effective amount of a pharmaceutical composition to the ocular surface of the individual of the individual. In specific embodiments, the pharmaceutical composition comprises a therapeutically effective amount of selenium disulfide ($SeS_2$). In some embodiments, the ocular surface is protected with a barrier prior to administering the pharmaceutical composition to the ocular surface. Alternatively and/or additionally, the ocular surface is protected with a barrier concurrently with the process of administering the pharmaceutical composition to the ocular surface. The barrier can be any physical or chemical barrier that is pre-formed before applying to the ocular surface. Alternatively and/or additionally, the barrier is formed on the ocular surface after being applied to the ocular surface.

In some instances, protecting of the ocular surface of the individual comprises administering an ointment, a polyvinyl alcohol (PVA) microemulsion, other micro or nano-emulsions of polymers, or liquid crystal form of polymers that can act as a barrier. Alternatively and/or additionally, protecting of the ocular surface of the individual comprises administering lipid or sugar based compound that can cover ocular surface or cornea. For example, such lipid or sugar based compound includes cross linked dextran or dense liposome. Alternatively and/or additionally, protecting of the ocular surface of the individual comprises administering a hyaluronic acid (HA), or any suitable HA-containing compound, which interacts with mucin on the ocular surface and/or the surrounding ocular tissues of the individual and forms a barrier. Preferably, such formed barrier prevents the photosensitized $SeS_2$ from contacting the ocular surface of an individual. While any suitable hyaluronic acid, hyaluronic acid polymer, or a HA-containing compound suitable to apply to the ocular surface are contemplated, preferred hyaluronic acid or hyaluronic acid polymer includes those with a molecular weight of at least 700 kDa, at least 800 kDa, at least 900 kDa, at least 1000 kDa, at least 1100 kDa, at least 1200 kDa, at least 1300 kDa, at least 1400 kDa, at least 1500 kDa, at least 2000 kDa, at least 2500 kDa, at least 3000 kDa, or at least 3500 kDa, or between 700-3500 kDa, 700-3000 kDa, 700-2500 kDa, 700-2000 kDa, 700-1500 kDa, 700-1300 kDa, or 700-1200 kDa.

In some instances, the protecting the ocular surface comprises administering an additive molecule to the ocular surface as a barrier. The additive molecule is configured to, suitable for, or capable of, capture a free radical or photosensitized $SeS_2$, so that the captured free radical or photosensitized $SeS_2$ does not reach, does not directly contact, thereby the adverse effect on the ocular surface is reduced. In some embodiments, the additive molecule, when applied to the ocular surface, capture at least 10%, at least 20%, at least 30%, at least 40%, at least 50%, at least 60%, at least 70% of the free radical or photosensitized $SeS_2$. In some instances, the additive molecule comprises one or more of a phenolic compound, vitamin E, vitamin C, carotenes, ferritin, ceruloplasmin, selenium, reduced glutathione (GSH), manganese, ubiquinone, zinc, flavonoids, coenzyme Q, melatonin, bilirubin, taurine, or cysteine. In some embodiments, the additive molecule is formulated with a suitable excipients (e.g., buffer, etc.) in any suitable form (e.g., gel, hydrogel, ointment, cream, lotion, foam, spray, patch, implant (e.g., slow release, biodegradable, semi-degradable, or non-degradable), lipid base systems (e.g., solid lipid nano/micro particles, liposomes, exosome, micelles, micro/nano emulsions, cubosomes, cochleatses, niosomes, lipospheres), silica based system (e.g., mesoporous), polymer based system, nano and/or micro-spheres, nano- and/or micro-capsules, nano- and/or micro-particles, or the like, etc.) to be applied on the ocular surface of the individual before administering the pharmaceutical composition (e.g., $SeS_2$-containing pharmaceutical composition). Alternatively and/or additionally, the additive molecule is added to the $SeS_2$-containing pharmaceutical composition such that the additive molecule can be applied to the ocular surface concurrently with the $SeS_2$-containing pharmaceutical composition.

In some instances, the barrier is a contact lens or any other types of transparent or nontransparent layer that creates a physical barrier on the ocular surface to protect the ocular surface from the photosensitized $SeS_2$ or other reactive oxygen species (i.e., generated from the photoreaction of $SeS_2$). The size of the contact lens or any other types of transparent or nontransparent layer varies depending on the area of the protection. For example, the size of the contact lens or any other types of transparent or nontransparent layer is determined to cover at least 40%, at least 50%, at least 60%, at least 70%, at least 80%, at least 90% of the ocular surface of the individual.

Such processes of protecting the ocular surface of the individual from the photosensitized $SeS_2$ or other reactive oxygen species with a barrier enables the $SeS_2$-containing pharmaceutical composition to be administered under a good or high-light condition (e.g., under sunlight, under a light having at least 50 lux or more, at least 100 lux or more, at least 500 lux or more, or at least 1,000 lux or more, etc.) by preventing or reducing the adverse effect of photosensitized $SeS_2$ or phototoxicity from other reactive oxygen species upon administration of the $SeS_2$-containing pharmaceutical composition. In addition, by preventing the access of the photosensitized $SeS_2$ or other reactive oxygen species to the ocular surface during administering the $SeS_2$-containing pharmaceutical composition, such administering step removes or at least reduces the need of further limitation, avoidance or instruction to limit or avoid exposure to light following the administration.

EXAMPLES

Example 1

In vivo rabbit study of preparations comprising $SeS_2$. In a preclinical study performed on rabbits, it is observed that a small dose of $SeS_2$ (about 4 mg) at a concentration of up to 2.5 wt. % is safe. This dose, provided in an ointment and applied over the eyelid margin, is well tolerated and does not produce keratitis in the individuals receiving treatment. Upon increasing the dose to about 20 mg, keratitis is observed in the test subjects. These findings are understood to indicate that keratitis and related side-effects of $SeS_2$ treatment may depend not only on the concentration of $SeS_2$, but also on the total dose.

Example 2

In a clinical study three different concentrations were used; 0.1 wt. %, (10 subjects) 0.5 wt. % (12 subjects) and 1 wt. % (26 subjects). Most applications were done bi-weekly while some patients moved to daily application based on prespecified protocol criteria. Of the subjects who participated in the study, four developed keratitis, keratitis related symptoms, or keratitis related symptoms. All four subjects were treated using the 1 wt. % concentration. In one instance, a patient was treated for a month and was improving according to multiple ophthalmic health metrics but developed keratitis after his 1-month visit to the office. During the 1-month visit, the patient applied the drug as part of the in-office assessment during the morning hours. About 7 hours later, the patient started to feel significant pain. Upon examination the next morning, the patient showed corneal staining in the form of a band at the interpalpebral fissure and was diagnosed with keratitis. The patient had no adverse events during the first month while applying the drug twice weekly (at home, before bedtime) and had a significant improvement in total ocular surface disease index (OSDI), visual analogue scale (VAS), and standard patient evaluation of eye dryness (SPEED). After resolution of the keratitis this patient continued dosing at bed time with no subsequent development of keratitis.

A surprising incidence of patients improving while applying the drug at home without any adverse effects, then developing keratitis several hours after applying it in the clinic was observed. This recurring pattern suggested a toxic reaction following in-office, daytime application of $SeS_2$. An additional three patients reported the initiation of pain between 6 and 20 hours after the application, indicating this indeed follows a pattern of toxic reaction. Two of the patients developed keratitis after the first application—a single application done during daytime in the office—which was done on the first day of the trial. The last subject developed keratitis after the in-office application done during day 14 of the study. This last subject, similar to the first patient, also applied the treatment at home on a bi-weekly basis without any adverse reaction.

The proposition that $SeS_2$ was reacting with light to cause a photosensitive reaction was informed by the following factors: (1) the consistent development of keratitis following an in-office, daytime application, (2) more than 400 bedtime applications of 1 wt. % $SeS_2$ being performed without a single occurrence of keratitis, and (3) the time course between a daytime application of 1 wt. % $SeS_2$ ointment and the development of symptoms of keratitis. Given that 0.1 wt. % and 0.5 wt. % in-office, daytime applications also occurred in 9 and 7 patients respectively with no development of keratitis, and given that keratitis developed in rabbits at the high dose of about 20 mg but not at low dose of about 4 mg, it is likely that this phenomenon is both dose- and concentration-related.

The duration of time the drug product can be visualized on the eye was also tested. It was concluded that after 5 hours, no drug product is visibly present.

$SeS_2$ (2.5 wt. %) can produce contact dermatitis, e.g., due to an irritant effect. As a treatment for tinea versicolor, Giordano once applied $SeS_2$ overnight (e.g., at night or before bedtime for overnight efficacy), not out of concern of sun exposure, but rather to allow its prolonged exposure to the skin. Robinson and Yaffe used $SeS_2$ cream (1 wt. %) for the same indication twice daily for 2 weeks. The 32 cases described by Robinson and Yaffe indicate that daytime exposure was not a concern, as it was recommended to take a shower only once every 3 days to remove the $SeS_2$ cream. None of the investigators encountered a single case of either contact dermatitis or photo-contact dermatitis, and there are no references to the potential phototoxic effect of $SeS_2$. In some instances, overnight application is important for lower concentrations of $SeS_2$, for example between about 0.1 wt. % and 2.5 wt. % (e.g., 0.5 wt. %).

In one instance, a patient applied $SeS_2$ shampoo for three consecutive nights as prescribed by a physician to treat asymptomatic, hypopigmented macules on the face, neck, and upper limbs. Five days after the third treatment, the patient developed circumscribed eczematous plaques on the light-exposed areas of the face, neck, and upper limbs. In some instances, dermatitis induced by $SeS_2$ is likely to be photoallergic, as the dermatitis developed five days after the last application. The minimum time for the sensitizing processes to be complete is five days. Moreover, phototoxic and primary irritant reactions are seen when the concentration of the photoreactive chemical is high. Such phototoxic or irritant reactions are unlikely to occur after a time lag following discontinuation of any topical medication. The previously described eczematous plaques developed primarily in sun-exposed areas despite the patient applying the shampoo all over the body, which indicates that the reaction was not a primary irritant dermatitis. Exacerbations on sun exposure even after 3 weeks also point in favor of an allergic mechanism. Photosensitive dermatitis as a side effect of medication typically subsides in one to two weeks following withdrawal of the offending agent and sunlight. In some instances, the offending agent may persist in the dermis, or a protein or cell may be altered, resulting in persistence of photosensitivity.

The development of photosensitivity in response to a selenium composition (e.g., $SeS_2$) stands in contrast to the known skin protective effects of some selenium compounds, especially with respect to UVA (radiation with a wavelength of about 320 nm to about 400 nm) exposure. The previously observed UVA-protective effects which may be facilitated by selenium's capacity to promote the synthesis of glutathione, a key component of fibroblasts and keratinocytes. In some instances, the contrast between UV-protective effects and photosensitivity may derive from selenium solubility. Prior data showing the UV-protective effect of selenium compounds typically correspond to soluble selenium compounds. The protective effect of selenium compounds starts at low doses. In the ophthalmic treatments described herein, the active compound is non-soluble selenium disulfide with minimal concentrations of soluble selenium (<5 ppm). The phototoxicity effect observed in one of the ophthalmic studies described herein are observed at concentrations at least as low as about 0.5 wt. % and 1 wt. %.

In some instances, certain concentration levels of $SeS_2$ may tip the balance between protective and sensitizing effects. In certain instances, high levels of non-soluble selenium may lead to phototoxicity due to elevated levels of glutathione or other proteins, inducing oxidative imbalance and cellular toxicity. This cellular toxicity and oxidative imbalance may be further elevated by UVA exposure.

Example 3

An additional 7 subject received 1 wt. % selenium disulfide in a manner similar to that described in Example 2. An additional 2 or 3 additional cases of adverse effects. Of these subjects, 2 had keratitis following the $1^{st}$ in-office application and another patient deteriorate following the $2^{nd}$ in-office application although the subject kept on another dose or two at home before coming with pain to be examined (a typical scenario when keratitis evolves).

Example 4

Human study of preparations comprising $SeS_2$. One of three concentrations of $SeS_2$ (0.1 wt. %, 0.5 wt. %, and 1 wt. %) is applied to a human subject in order to determine safety and efficacy. The treatment, an ointment-based $SeS_2$ composition, is applied over the eyelid margin by the individual receiving treatment (i.e., self-administration). In most instances, the treatment is applied on a biweekly basis, however some patients move to daily application based on prespecified protocol criteria. Because the ointment-based composition is known to mix with tear fluid and cause blurry vision, individuals in this study are advised to apply the treatment prior to bed so as to avoid risks associated with reduced vision acuity. An additional component of the study requires individuals to apply the ointment in the presence of an ophthalmologist in order to demonstrate proper self-administration technique consistent with the designed study. The in-office applications are conducted at specific, predetermined time points. In these instances, the treatment is not applied before bed but rather is performed during daylight hours.

Keratitis is not observed in any patients receiving treatment at either the 0.1 wt. % or the 0.5 wt. % concentration. However, four patients note symptoms of keratitis in the 1 wt. % concentration cohort. It should be noted that all four patients describing symptoms of keratitis do so following the prescribed in-office assessment whereas none of the 400 or more bedtime applications of treatment results in keratitis. Prior to the in-office assessment whereafter keratitis develops, at least one patient demonstrates improved health outcomes following one month of treatment as measured by total ocular surface disease index (OSDI), visual analogue scale (VAS), and standard patient evaluation of eye dryness (SPEED). However, within 7 hours of performing the in-office assessment, the patient describes significant pain near the treated area. Subsequent corneal staining with fluorescein indicates keratitis, observed in the form of a band at the interpalpebral fissure.

At least three other individuals show symptoms of keratitis following a pattern consistent with the first described individual. All four individuals report the initiation of pain between 6 and 20 hours of the in-office assessment, i.e., a 1 wt. % concentration of $SeS_2$ is applied. This pattern of occurrence suggests a correlation between the development of keratitis and both context in which treatment is administered as well as the concentration of treatment administered.

Determination of time period that treatment is visibly present. The duration of time during which the drug product is visibly present on or near the eye of an individual is assessed. Investigators conclude that drug product is no longer visibly present after 5 hours.

Example 5

An analysis of masked data in two ongoing studies using the same concentration of $SeS_2$ (i.e., 0.5%) at overlapping sites indicates a clear and unexpected tolerability advantage for dosing the drug product only at night. In a first study patients were instructed to dose in both the evening, between visits, and in the daytime during regular scheduled clinic visits as part of the study protocol. Study patients received a 2-week run-in on a placebo which was administered twice weekly for a period of two weeks. Upon meeting inclusion/exclusion criteria, the patients were randomized to be administered an $SeS_2$ ointment/semi-solid drug (i.e., 0.1%, 0.5%, or 1.0%) or a placebo for a dosing regimen comprising either a twice-week administration for three months or a once daily dosing for three months.

In a second study is almost identical to the first study, but all daytime visits were eliminated, the ointment/semi-solid $SeS_2$ (e.g., 0.5%) was administered twice weekly in the evening at bedtime for three months. There was a clear and significant reduction in ocular adverse events in the second (night time administration only) study relative to the first study (reduction of 75% in the incidence of adverse events). Adverse events comprise a feeling of grittiness, foreign body feeling, stinging, blurry vision, redness, tired eyes, water eyes, irritation, lid abnormalities, burning, corneal abrasion, photophobia, staining, or dry eye disorder (DED). Adverse events consist mainly of events associated with tolerability such as burning and stinging after application.

The rates of ocular adverse events (ocular AE) and more importantly discontinuations from adverse events (DC for AE, that are mostly related to ocular tolerability) appear to be reduced by at least 50% when allowing dosing only in the evening rather than the AM.

Example 6

In a study testing the efficacy of $SeS_2$ in meibomian gland disorder (MGD) patients, subjects were allowed to choose between their finger or a cotton wool applicator (e.g., swab) to apply the ointment over the lid margin Of the 22 meibomian gland disorder (MGD) patients, 9 elected to use their finger while 13 used the applicator. The drug was applied twice a week and final evaluation was done at the 3 month time point in which the primary outcome of Meibomian Gland Score (MGS) was assessed. The average change from baseline in MGS in the 9 patients who use their finger was 10 (+/−8.2) vs. 2.3 (+/−4.4) in the 13 patients who used the applicator. This difference was statistically significant (p=0.03). Typically creams, cosmetics and ointments used on the lid margin are applied using an applicator and hence it was an unexpected finding that using a finger enhances the efficacy of the drug.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for treating a disease or disorder in or around an eye of an individual in need thereof, the method comprising:

administering a therapeutically effective amount of a pharmaceutical composition to an ocular surface, surrounding ocular tissues, or a combination thereof of the individual;

wherein the pharmaceutical composition comprises a therapeutically effective amount of selenium disulfide ($SeS_2$); and wherein the pharmaceutical composition is administered at bedtime or within an hour of bedtime.

2. The method of claim 1, wherein the disease or disorder in or around the eye is dry eye syndrome.

3. The method of claim 2, wherein the individual has meibomian gland dysfunction (MGD).

4. The method of claim 3, wherein the pharmaceutical composition is administered at bedtime.

5. The method of claim 4, wherein the pharmaceutical composition is applied to an eyelid margin of the individual.

6. The method of claim 5, wherein the pharmaceutical composition is administered to the individual in a volume of less than about microliters ($\mu L$).

7. The method of claim 1, wherein the individual applies a volume of less than about 25 $\mu L$ of the pharmaceutical composition to an eyelid margin of the individual.

8. The method of claim 1, wherein the pharmaceutical composition comprises selenium disulfide in a therapeutically effective concentration.

9. The method of claim 8, wherein the therapeutically effective concentration is about 0.5 by weight (wt. %).

10. The method of claim 9, wherein the individual applies a volume of less than about 25 $\mu L$ of the pharmaceutical composition to an eyelid margin of the individual.

11. The method of claim 10, wherein the disease or disorder in or around the eye of the individual in need thereof is dry eye syndrome and the individual has MGD.

12. The method of claim 1, wherein the disease or disorder in or around the eye is meibomian gland dysfunction (MGD).

13. The method of claim 1, wherein the disease or disorder in or around the eye is meibomian gland dysfunction (MGD) and the individual has signs and symptoms of dry eye disease.

14. The method of claim 13, wherein the pharmaceutical composition is applied to an eyelid of the individual.

15. The method of claim 14, wherein the individual applies a volume of less than about 25 $\mu L$ of the pharmaceutical composition to an eyelid margin of the individual at bedtime.

16. The method of claim 15, wherein the pharmaceutical composition comprises selenium disulfide in an amount of about 0.5 by weight (wt. %) to about 1.0% wt. %.

17. The method of claim 1, wherein the individual has signs and symptoms of dry eye disease.

18. The method of claim 1, wherein the individual has meibomian gland dysfunction (MGD).

19. The method of claim 1, wherein the individual has meibomian gland dysfunction (MGD) and sins and symptoms of dry eye disease.

20. The method of claim 18, wherein the pharmaceutical composition is applied to an eyelid of the individual.

21. The method of claim 20, wherein the individual applies a volume of less than about 25 $\mu L$ of the pharmaceutical composition to an eyelid margin of the individual at bedtime.

22. The method of claim 18, wherein the pharmaceutical composition comprises selenium disulfide in an amount of about 0.5 by weight (wt. %) to about 1.0% wt. %.

23. The method of claim 1, wherein the pharmaceutical composition is applied to an eyelid of the individual.

24. The method of claim 23, wherein the individual applies a volume of less than about 25 $\mu L$ of the pharmaceutical composition to the eyelid of the individual.

25. The method of claim 24, wherein the pharmaceutical composition comprises selenium disulfide in an amount of about 0.5 by weight (wt. %) to about 1.0% wt. %.

26. The method of claim 1, wherein the pharmaceutical composition is administered to the individual in a volume of less than about 25 microliters ($\mu L$) at bedtime.

27. The method of claim 26, wherein the pharmaceutical composition comprises selenium disulfide in an amount of about 0.5 wt. %.

28. The method of claim 27, wherein the individual applies the pharmaceutical composition to an eyelid margin of the individual.

29. The method of claim 1, wherein the pharmaceutical composition comprises selenium disulfide in an amount of about 0.5 by weight (wt. %) to about 1.0% wt. %.

30. The method of claim 29, wherein the pharmaceutical composition comprises selenium disulfide in an amount of about 0.5 wt. %.

31. The method of claim 30, wherein the pharmaceutical composition the individual applies a volume of less than about 25 $\mu L$ of the pharmaceutical composition.

32. The method of claim 31, wherein the pharmaceutical composition is applied to an eyelid margin of the individual at bedtime.

* * * * *